US006994976B1

(12) United States Patent
Tittle et al.

(10) Patent No.: US 6,994,976 B1
(45) Date of Patent: Feb. 7, 2006

(54) TR3-SPECIFIC BINDING AGENTS AND METHODS FOR THEIR USE

(76) Inventors: Thomas V. Tittle, 7123 N. Oatman Ave., Portland, OR (US) 97217; Keith W. Wegmann, 15916 NE. 40th St., Vancouver, WA (US) 98682

( * ) Notice: Subject to any disclaimer, the term of this patent is extended or adjusted under 35 U.S.C. 154(b) by 0 days.

(21) Appl. No.: 10/204,419

(22) PCT Filed: Nov. 17, 2000

(86) PCT No.: PCT/US00/31692

§ 371 (c)(1),
(2), (4) Date: Aug. 29, 2002

(87) PCT Pub. No.: WO01/35995

PCT Pub. Date: May 25, 2001

Related U.S. Application Data

(60) Provisional application No. 60/166,583, filed on Nov. 19, 1999.

(51) Int. Cl.
  G01N 33/53    (2006.01)
  G01N 33/567   (2006.01)
  C07K 16/00    (2006.01)
  A61K 38/00    (2006.01)
(52) U.S. Cl. .................... 435/7.1; 435/7.21; 435/7.23; 435/7.24; 530/387.1; 530/388.1; 530/389.1; 514/2
(58) Field of Classification Search ................. 435/7.1, 435/7.21, 7.23, 7.24; 530/387.1, 388.1, 389.1; 514/2
See application file for complete search history.

(56) References Cited

U.S. PATENT DOCUMENTS 6,462,176 B1 * 10/2002 Ashkenazi .................. 530/350

FOREIGN PATENT DOCUMENTS

| WO | WO 97 33904 | 9/1997 |
| WO | WO 97 37020 | 10/1997 |
| WO | WO 98 05783 | 2/1998 |
| WO | WO 99/19490 | * 4/1999 |
| WO | WO 00 64465 | 11/2000 |

OTHER PUBLICATIONS

Screaton, G. et al. Proc. Nat. Acad. Sci. 1997, vol. 94, pp. 4615-1619.*
Chicheportiche, Y., et al., "TWEAK, a new secreted ligand in the tumor necrosis factor family that weakly inducus apoptosis" (1997) *J. Bio Chem.* 272(51): 32401-32410.
Chicheportiche, Y., et al., "Proinflammatory activity of TWEAK on human dermal fibroblasts and synoviocytes: blocking and enhancing effects of anti-TWEAK monoclonal antibodies" (2002) *Arthritis Res.* 4(2): 126-133.
Donohue, P.J., et al., "TWEAK is an endothelial cell growth and chemotactic factor that also potentiates FGF-2 and VEGF-A mitogenic activity" (2003) *Arterioscler. Thromb Vasc. Biol.* 23(4): 594-600.
Kaplan, M.J., et al., "TRAIL (Apo2 ligand) and TWEAK (Apo3 ligand)mediate CD4+T cell killing of antigen-presenting macrophages" *J. Immunol* 164(6): 2897-2904.
Kaptein, A., et al., "Studies on the interaction between TWEAK and the death receptor WSL-1/TRAMP (DR3)" (2000) *FEBS lett.* 485(2-3): 135-141.
Marsters, S. A., et al., "Identification of a ligand for the death-domain-containing receptor Apo3" (1998) *Curr Biol.* 8(9): 525-528.
Nakayama, M., et al., "Characterization of murine TWEAK and its receptor (Fn14) by monoclonal antibodies" (2003) *Biochem Biophys Res Commun* 306(4): 819-825.
Polek., et al. "TWEAK mediates signal transduction and differentiation of RAW264.7 cells in the absence of Fn14/TWEAKR. Evidence for a second TWEAK receptor" (2003) *J. Bio Chem.*
Schneider, P., et al., "TWEAK can induce cell death via endogenous TNF and TNF receptor 1" (1999) *Eur J Immunol* 29(6): 1785-1792.
Wiley, S.R., et al., "A novel TNF receptor family member binds TWEAK and its implicated in angiogenesis" (2001) *Immunity* 15(5): 837-846.
International Search Report dated May 10, 2001.

* cited by examiner

*Primary Examiner*—Janet Andres
(74) *Attorney, Agent, or Firm*—Antoinette F. Konski

(57) ABSTRACT

Biologically active TR3-specific binding agents and methods for their use are disclosed. The biologically active TR3-specific binding agents are useful for inhibiting the proliferation of cells expressing TR3. These biologically active agents are particularly useful for treating T-cell mediated diseases such as graft-versus-host disease, organ rejection, tumor growth, autoimmunity, and inflammation.

14 Claims, 19 Drawing Sheets

A  Unstimulated
B  Con A Stimulated, Untreated
C  Con A Stimulated, TR3 μk-1 Treated
D  Molecular Weight Stds

SEQUENCE LISTING

<160> NUMBER OF SEQ ID NOS: 7

<210> SEQ ID NO 1
<211> LENGTH: 1250
<212> TYPE: DNA
<213> ORGANISM: Homo sapiens

<400> SEQUENCE: 1

```
atggagcagc ggccgcgggg ctgcgcggcg gtggcggcgg cgctcctcct ggtgctgctg      60
ggggcccggg cccagggcgg cactcgtagc cccaggtgtg actgtgccgg tgacttccac     120
aagaagattg gtctgttttg ttgcagaggc tgcccagcgg ggcactacct gaaggcccct     180
tgcacggagc cctgcggcaa ctccacctgc cttgtgtgtc cccaagacac cttcttggcc     240
tgggagaacc accataattc tgaatgtgcc cgctgccagg cctgtgatga gcaggcctcc     300
caggtggcgc tggagaactg ttcagcagtg gccgacaccc gctgtggctg taagccaggc     360
tggtttgtgg agtgccaggt cagccaatgt gtcagcagtt caccttcta ctgccaacca     420 tgcctagact gcggggccct gcaccgccac acacggctac tctgttcccg cagagatacg     480
actgtgggac ctgcctgcct ggcttctatg aacatggcga tggctgcgtg tcctgcccca     540
cgagcaccct ggggagcgtc cagagcgctg tgccgctgtc tgtggctgga ggcagatgtt     600
ctgggtccag gtgctcctgg ctggccttgt ggtcccctc ctgcttgggg ccaccctgac     660
ctacacatac cgccactgct ggcctcacaa gcccctggtt actgcagatg aagctggagg     720
aggctctgac cccaccaccg gccacccatc tgtcacccct ggacagcgcc cacacccttc     780
tagcacctcc tgacagcagt gagaagatct gcaccgtcca gttggtgggt aacagctgga     840
cccctggcta ccccgagacc caggaggcgc tctgcccgca ggtgacatgg tcctgggacc     900
agttgcccag cagagctctt ggccccgctg ctgcgcccac actctcgcca gagtcccag     960 ccggctcgcc agccatgatg ctgcagccgg gcccgcagct ctacgacgtg atggacgcgg    1020
tcccagcgcg gcgctggaag gagttcgtgc gcacgctggg gctgcgcgag gcagagatcg    1080
aagccgtgga ggtggagatc ggccgcttcc gagaccagca gtacgagatg ctcaagcgct    1140
ggcgccagca gcagcccgcg ggcctcggag ccgtttacgc ggccctggag cgcatggggc    1200
tggacggctg cgtggaagac ttgcgcagcc gcctgcagcg cggcccgtga              1250
```

<210> SEQ ID NO 2
<211> LENGTH: 418
<212> TYPE: PRT
<213> ORGANISM: Homo sapiens

<400> SEQUENCE: 2

```
Met Glu Gln Arg Pro Arg Gly Cys Ala Ala Val Ala Ala Ala Leu Leu
 1               5                  10                  15
```

```
Leu Val Leu Leu Gly Ala Arg Ala Gln Gly Gly Thr Arg Ser Pro Arg
             20                  25                  30
Cys Asp Cys Ala Gly Asp Phe His Lys Lys Ile Gly Leu Phe Cys Cys
             35                  40                  45
Arg Gly Cys Pro Ala Gly His Tyr Leu Lys Ala Pro Cys Thr Glu Pro
 50                  55                  60
Cys Gly Asn Ser Thr Cys Leu Val Cys Pro Gln Asp Thr Phe Leu Ala
 65                  70                  75                  80
Trp Glu Asn His His Asn Ser Glu Cys Ala Arg Cys Gln Ala Cys Asp
                 85                  90                  95
Glu Gln Ala Ser Gln Val Ala Leu Glu Asn Cys Ser Ala Val Ala Asp
                100                 105                 110
Thr Arg Cys Gly Cys Lys Pro Gly Trp Phe Val Glu Cys Gln Val Ser
             115                 120                 125
Gln Cys Val Ser Ser Ser Pro Phe Tyr Cys Gln Pro Cys Leu Asp Cys
130                 135                 140
Gly Ala Leu His Arg His Thr Arg Leu Leu Cys Ser Arg Arg Asp Thr
145                 150                 155                 160
Asp Cys Gly Thr Cys Leu Pro Gly Phe Tyr Glu His Gly Asp Gly Cys
             165                 170                 175
Val Ser Cys Pro Thr Ser Thr Leu Gly Ser Cys Pro Glu Arg Cys Ala
             180                 185                 190
Ala Val Cys Gly Trp Arg Gln Met Phe Trp Val Gln Val Leu Leu Ala
             195                 200                 205
Gly Leu Val Val Pro Leu Leu Leu Gly Ala Thr Leu Thr Tyr Thr Tyr
             210                 215                 220
Arg His Cys Trp Pro His Lys Pro Leu Val Thr Ala Asp Glu Ala Gly
225                 230                 235                 240
Met Glu Ala Leu Thr Pro Pro Ala Thr His Leu Ser Pro Leu Asp
                245                 250                 255
Ser Ala His Thr Leu Leu Ala Pro Pro Asp Ser Ser Glu Lys Ile Cys
             260                 265                 270
Thr Val Gln Leu Val Gly Asn Ser Trp Thr Pro Gly Tyr Pro Glu Thr
             275                 280                 285
Gln Glu Ala Leu Cys Pro Gln Val Thr Trp Ser Trp Asp Gln Leu Pro
290                 295                 300
Ser Arg Ala Leu Gly Pro Ala Ala Pro Thr Leu Ser Pro Glu Ser
305                 310                 315                 320
Pro Ala Gly Ser Pro Ala Met Met Leu Gln Pro Gly Pro Gln Leu Tyr
                325                 330                 335
Asp Val Met Asp Ala Val Pro Ala Arg Arg Trp Lys Glu Phe Val Arg
                340                 345                 350
Thr Leu Gly Leu Arg Glu Ala Glu Ile Glu Ala Val Glu Val Glu Ile
             355                 360                 365
Gly Arg Phe Arg Asp Gln Gln Tyr Glu Met Leu Lys Arg Trp Arg Gln
             370                 375                 380
Gln Gln Pro Ala Gly Leu Gly Ala Val Tyr Ala Ala Leu Glu Arg Met
385                 390                 395                 400
Gly Leu Asp Gly Cys Val Glu Asp Leu Arg Ser Arg Leu Gln Arg Gly
                405                 410                 415
Pro Glx
```

<210> SEQ ID NO 3

```
<211> LENGTH: 13
<212> TYPE: PRT
<213> ORGANISM: Homo sapiens

<400> SEQUENCE: 3

Gln Gly Gly Thr Arg Ser Pro Arg Cys Asp Cys Ala Gly
 1               5                  10

<210> SEQ ID NO 4
<211> LENGTH: 32
<212> TYPE: PRT
<213> ORGANISM: Homo sapiens

<400> SEQUENCE: 4

Gly Gly Gly Thr Arg Ser Pro Arg Cys Asp Cys Ala Gly Asp Phe His
 1               5                  10                  15

Lys Lys Ile Gly Leu Phe Cys Cys Arg Gly Cys Pro Ala Gly His Tyr
             20                  25                  30

<210> SEQ ID NO 5
<211> LENGTH: 7
<212> TYPE: PRT
<213> ORGANISM: Homo sapiens
<220> FEATURE:
<221> NAME/KEY: BINDING
<222> LOCATION: (1)...(1)
<223> OTHER INFORMATION: Ser or Thr
<220> FEATURE:
<221> NAME/KEY: BINDING
<222> LOCATION: (7)...(7)
<223> OTHER INFORMATION: Glu or Asp
<220> FEATURE:
<221> NAME/KEY: BINDING
<222> LOCATION: (2)...(6)
<223> OTHER INFORMATION: any amino acid
<220> FEATURE:
<221> NAME/KEY: VARIANT
<222> LOCATION: 1, 2, 3, 4, 5, 6, 7
<223> OTHER INFORMATION: Xaa = Any Amino Acid

<400> SEQUENCE: 5

Xaa Xaa Xaa Xaa Xaa Xaa Xaa
 1               5

<210> SEQ ID NO 6
<211> LENGTH: 13
<212> TYPE: PRT
<213> ORGANISM: Homo sapiens

<400> SEQUENCE: 6

His Cys Leu Gly Lys Trp Leu Gly His Pro Asp Lys Phe
 1               5                  10

<210> SEQ ID NO 7
<211> LENGTH: 19
<212> TYPE: PRT
<213> ORGANISM: Homo sapiens

<400> SEQUENCE: 7

Asp Phe His Lys Lys Ile Gly Leu Phe Cys Cys Arg Gly Cys Pro Ala
 1               5                  10                  15

Gly His Tyr
```

TR3-SPECIFIC BINDING AGENTS AND METHODS FOR THEIR USE

CROSS-REFERENCE TO RELATED APPLICATION

This application claims priority under 35 U.S.C. § 119(e) to U.S. Provisional Application Ser. No. 60/166,583, filed Nov. 19, 1999, the contents of which are incorporated herein by reference.

FIELD OF THE INVENTION

This invention relates generally to biological cell-surface antigens and agents that bind to such antigens. More specifically, this invention relates to biologically active TR3-specific binding agents and to methods for using such TR3-specific binding agents.

BACKGROUND OF THE INVENTION

Structural Characteristics of TR3

TR3 (also known as Apo-3, DR3, LARD, Tramp, and WSL-1) is a member of the tumor necrosis factor receptor (TNFR) superfamily of cell-surface antigens. Some members of this superfamily (e.g., NGFR (nerve growth factor receptor), and CD95 (Fas/APO-1)) have broad tissue distribution, while other members of the superfamily (e.g., CD27, CD30, CD40, CD134, 4-1BB, and TR3) are restricted to cells of the lymphoid/hematopoietic system. Except for TR3, this latter group of receptors has been associated with the up-regulation of cell proliferation. TR3 possesses a cytoplasmic death domain homologous to TNFR and CD95 and is thought to be involved in programmed cell death (apoptosis).

Each of these receptors interacts with a cell-surface ligand. In the case of the lymphoid members of this superfamily, the ligands are usually expressed on a complimentary cell type. That is to say, if the receptor is on a T-cell, the ligand is found on an antigen-presenting cell (APC, such as B-cells, macrophages, or dendritic cells) and vice versa. The interaction between these receptor/ligand pairs is thought to deliver signals for activation or death to the receptor bearing cell. To date, the ligand for TR3 has not been discovered.

Role of Activated T-cells in Disease

T lymphocytes are the major cause of graft-versus-host disease (GVHD). Prophylaxis of GVHD is achieved by administering one or more pan T-cell immunosuppressive agents such as cyclosporin, corticosteroids, or methotrexate. These immunosuppressive agents are termed "pan" immunosuppressive agents because they suppress B-cells, T-cells, and the precursor T lymphocytes. It is not uncommon for subjects receiving such immunosuppressive agents to be immunocompromised for three months or more, leaving the subject with <1% normal levels of circulating T-cells. Thus, these agents are associated with significant subject morbidity and mortality due to secondary infection arising from a resulting absence of a functional immune system. Therefore, the development of therapeutic agents that can selectively limit the proliferation of activated T-cells is desirable.

Such therapeutic agents would also be of significant value in halting or at least slowing the progression of other diseases associated with T-cell proliferation, such as, acute and chronic transplantation-rejection diseases (graft-versus-host disease and organ rejection), autoimmune diseases (myasthenia gravis, systemic lupus erythematosus, rheumatoid arthritis, diabetes, multiple sclerosis, sarcoidosis, myocarditis, thyroiditis and other organ-specific autoimmune diseases), inflammatory diseases (toxic shock syndrome, inflammatory bowel disease and delayed-type hypersensitivity) and cancer (leukemia and lymphoma).

Potential Use of Antibodies to Fas

One proposed therapeutic agent for down-regulating the T-cell immune response was the use of antibodies directed towards Fas (also known as Apo-1 and CD95), a TNFR cell surface protein. Fas is expressed on activated normal human lymphoid cells and lymphoid tumor cells, including B-cells and T-cells, as well as other normal cells. The binding of anti-Fas antibodies to Fas causes growth inhibition and/or apoptosis of cells expressing Fas. Therefore, monoclonal antibodies to Fas were thought to be potentially therapeutically useful for controlling autoimmune diseases, as well as for controlling tumors that express Fas (U.S. Pat. No. 5,891,434 to Krammer, et al., filed Mar. 23, 1995).

Unfortunately, subsequent to the filing of the Krammer et al. patent application, Fas has been found to have a wide tissue distribution which makes it an unlikely candidate for the selective control of the T-cell immune response. Injection of anti-Fas antibodies into wild-type mice caused rapid death of the mice. Autopsies revealed severe damage to the liver by apoptosis. Ogasawara et al., *Nature*, 364:806–809, 1993.

DISCLOSURE OF THE INVENTION

The present invention stems from a discovery that TR3 is expressed selectively on activated T-cells and on some tumor cells. This discovery is particularly important for the use of monoclonal antibodies (McAbs) to TR3 and other biologically active TR3-specific binding agents as selective immunosuppressive agents. The traditional method of producing McAbs requires the presence of activated T-cells in the animal. However, because TR3-specific McAbs bind to and inhibit the proliferation of activated T-cells, the activated T-cells are not available to provide the help to B-cells required to produce McAbs. Hence, the discovery that TR3 is expressed on activated T-cells required the development of alternative methods of creating biologically active TR3-specific binding agents, such as McAbs.

Furthermore, the discovery that TR3 is selectively expressed on activated T-cells and the creation of biologically active TR3-specific McAbs offer a viable alternative to using antibodies such as the anti-Fas antibodies, described above. These biologically active TR3-specific McAbs selectively bind to activated T-cells, as well as to tumor cells derived from lymphoid tissue, and inhibit the proliferation of cells expressing TR3. This allows the selective elimination of activated T-cells and T-cell tumors. This would leave the rest of the immune system unharmed, thereby providing a unique mode of treatment.

Accordingly, one aspect of the invention provides biologically active TR3-specific binding agents that selectively bind to TR3 and inhibit the proliferation of cells expressing TR3. Examples of such biologically active specific binding agents include, but are not limited to, McAbs to TR3 (including various isotypes of such McAbs), polyclonal antibodies to TR3, mimetics of these antibodies, natural ligands of TR3-specifc binding agents, and various fragments and derivatives of TR3-specific binding agents.

Another aspect of the invention provides methods for making biologically active TR3-specific binding agents. These methods involve utilizing T-cell help from a source other than immune B-cell donors. T-cell help refers to interactions with T-cells by direct contact or through secretion of cytokines by T-cells; such interactions stimulate B-cells to secrete antibodies. An example method involves using a TR3-specific T-cell line to supply T-cell help to B-cells from a TR3-primed donor, and then fusing the resulting activated B-cells with lymphoid cells to create a hybridoma that produces biologically active TR3-specific McAbs.

Yet another aspect of the invention provides methods for detecting biologically active TR3-specific binding agents. The methods involve contacting at least one TR3-specific binding agent with at least one activated T-cell or T-cell tumor and determining the resulting level of T-cell proliferation. A diminution of T-cell proliferation indicates that the TR3-specific binding agent is biologically active. This method can be practiced in vivo and in vitro. Accordingly, another aspect of the invention is the generation of biologically active TR3-specific binding agents identified by this method.

Another aspect of the invention provides methods for treating subjects suspected of having a disease associated with an unwanted proliferation of cells expressing TR3, e.g., a T-cell mediated disease. An example method involves administering to the subject at least one biologically active TR3-specific binding agent. This method is particularly useful for treating a subject about to receive, or that just received, an allogeneic bone marrow transplant and that may suffer from GVHD. This method is also useful for treating tumors, organ transplant rejection, autoimmune diseases, allergy, toxic shock syndrome and inflammatory diseases.

Although the rats exhibited a good primary response to the TR3 peptide, they failed to respond to a secondary challenge, suggesting that antibodies produced by the immunized rats have eliminated T-cell help for the TR3 peptide.

Figure 8:
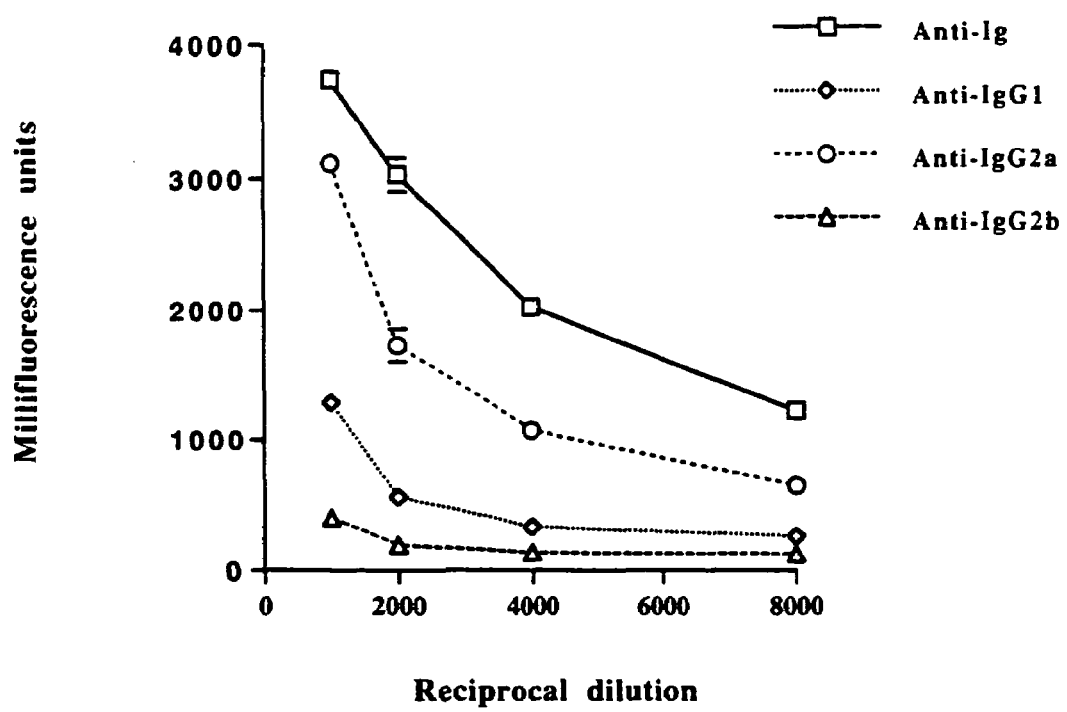

FIG. 8 sows that rats exhibiting an anti-TR3 immune response can exhibit isotype switching. Rats were immunized with the TR3 (1–32) peptide and rested. After 12 weeks, sera were collected from the rats and analyzed for various immunoglobulin isotypes at the designated dilutions. IgG1 and IgG2a, and to a lesser extent IgG2b, were all present, indicating that isotype switching occurred.

Figure 9:
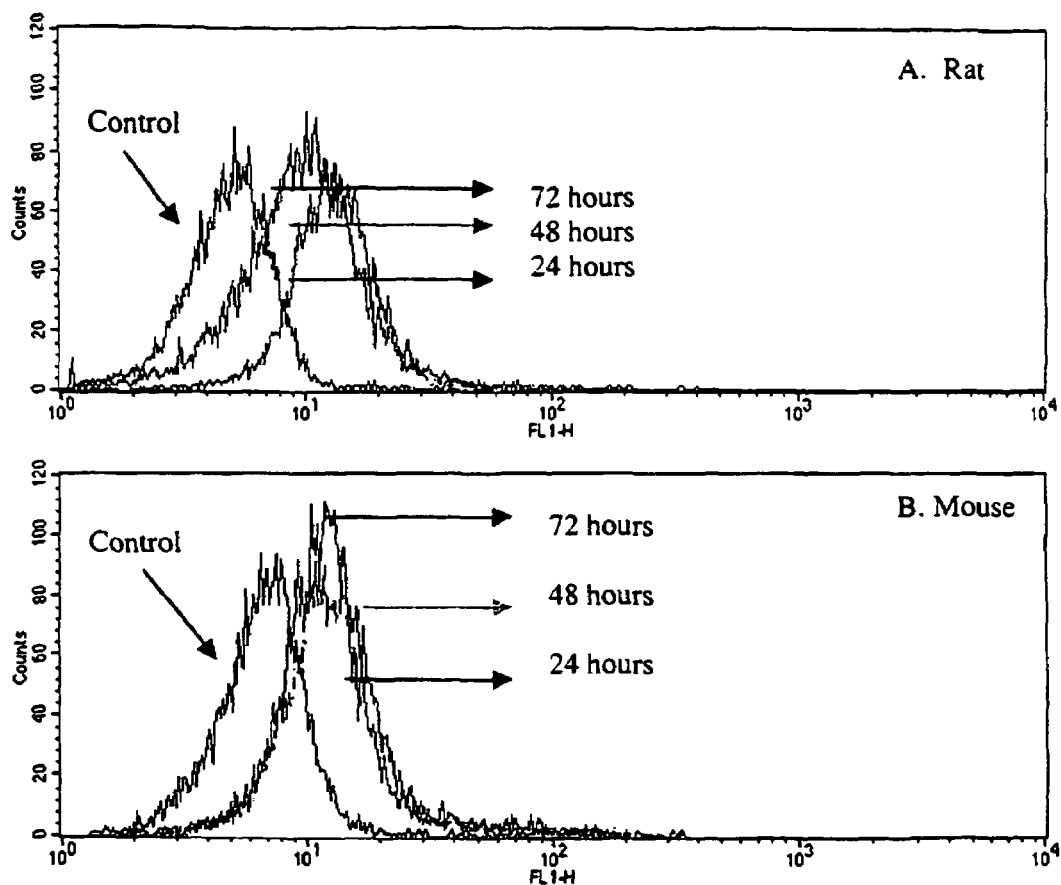

FIG. 9 shows that TR3 expression is induced on the surface of rat and murine CD4$^+$ T-cells after antigen stimulation. T-cell lines were stimulated in vitro with 1 μg/mL bovine MBP or with 2 μg/mL murine PLP (proteolipid protein) amino acids 139–151 for rat (A) and mouse (B), respectively. The expression of TR3 was detected at 24 hours with equivalent staining at 48 hours and 72 hours post-stimulation relative to unstained CD4+ T-cells.

Figure 10:
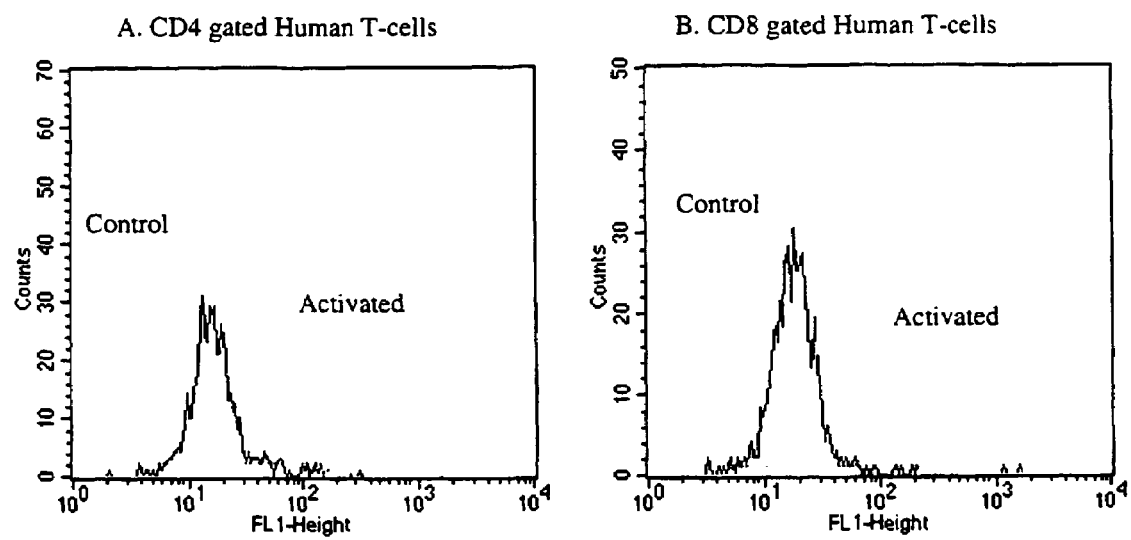

FIG. 10 shows that TR3 is expressed on human CD4+ and CD8+ T-cells at 72 hours post allostimulation with Epstein Barr virus-1 (EBV-1) stimulator cells. The human Allo-1 cell line was cultured alone ("Control") or with EBV-1 cells as stimulators ("Activated"). After 72 hours, cells were harvested and stained with anti-CD4:PE (plot A) or anti-CD8:PE (plot B) and counterstained with anti-TR3:FITC. Some of the CD4+-stained cells were double-stained with anti-TR3 (plot A), or some of the CD8+-stained cells were double-stained with anti-TR3 (plot B). The histograms were generated by selecting either CD4+ (plot A), or CD8+ (plot B) T-cells.

Figure 11:
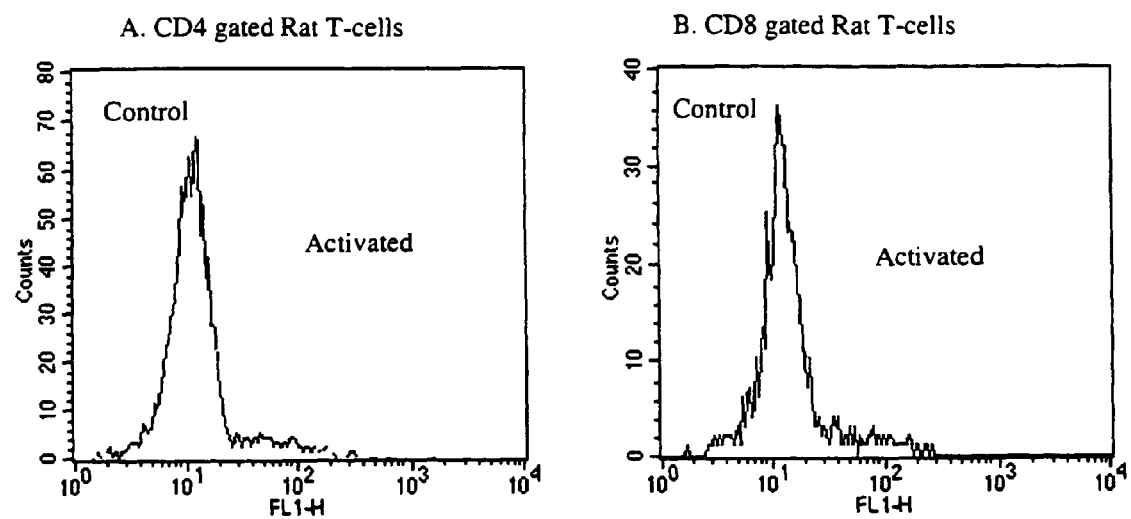

FIG. 11 shows that TR3 is expressed on CD4+ and CD8+ rat lymph node T-cells activated with anti-CD3 antibodies (CD3 is expressed on T-cells, is associated with the T-cell antigen receptor, and facilitates signal transduction) and anti-CD28 antibodies (CD28 is expressed on T-cells, and is responsible for co-stimulating naïve T-cells). Rat lymph node T-cells were cultured alone ("Control") or in the presence of anti-CD3 and anti-CD28 antibodies ("Activated"). After 48 hours, the cells were harvested and stained with anti-CD4:PE (plot A) or anti-CD8:PE (plot B), and counterstained with anti-TR3:FITC. The histograms were generated by selecting either CD4+ (plot A), or CD8+ (plot B) T-cells.

Figure 12:
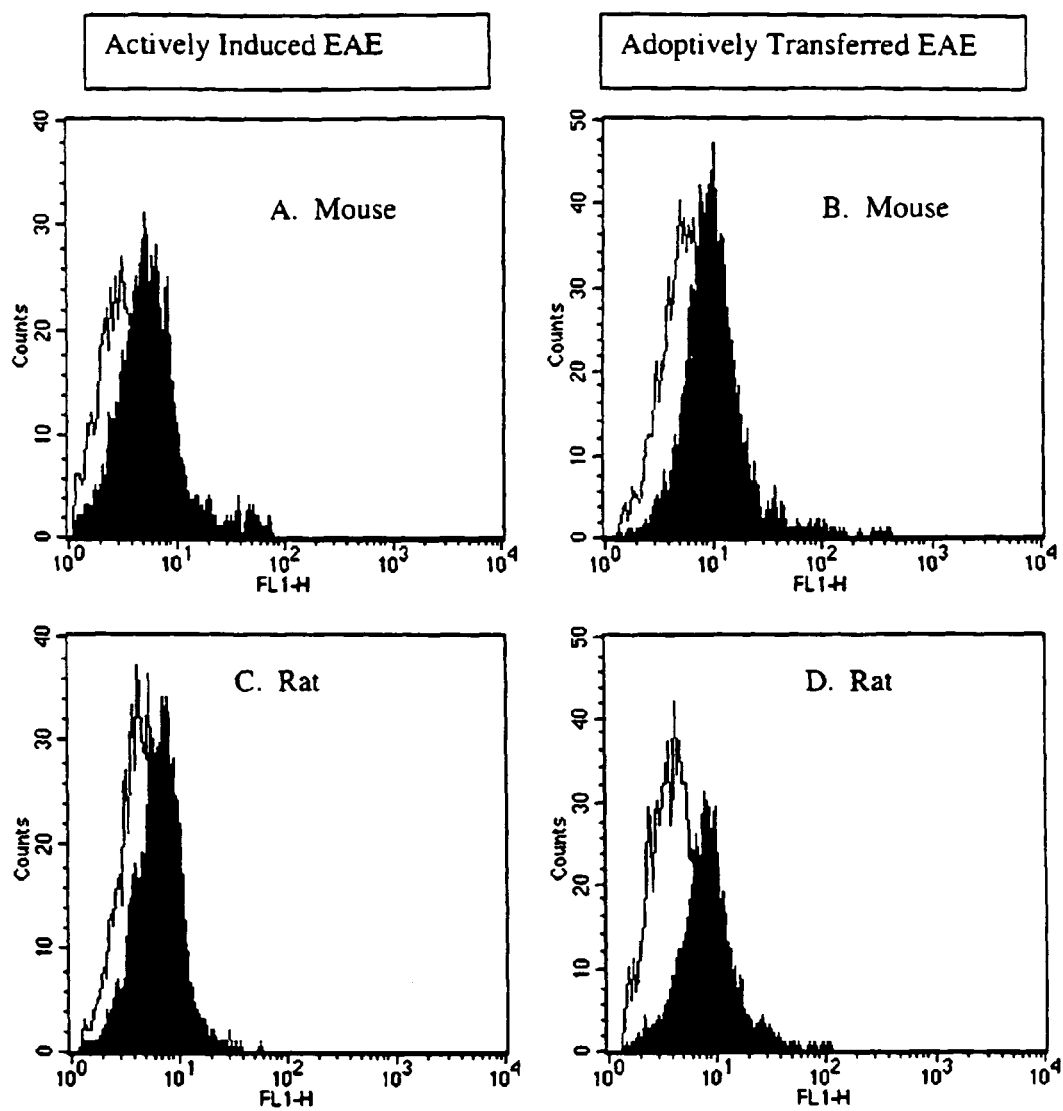

FIG. 12 shows that TR3 is expressed on CD4+ T-cells from the brains of rats and mice with active and adoptive EAE (experimental allergic encephalomyelitis). Mice and rats were either immunized to induce active EAE (plots A and C) or given $5 \times 10^6$ (plot B) or $2 \times 10^6$ (plot D) encephalitogenic T-cells for induction of adoptive EAE. On the day of disease onset, T-cells were isolated from the brain and stained with rat anti-mouse Vβ14 (open plots, isotype control) or with anti-TR3 (closed plots).

Figure 13:
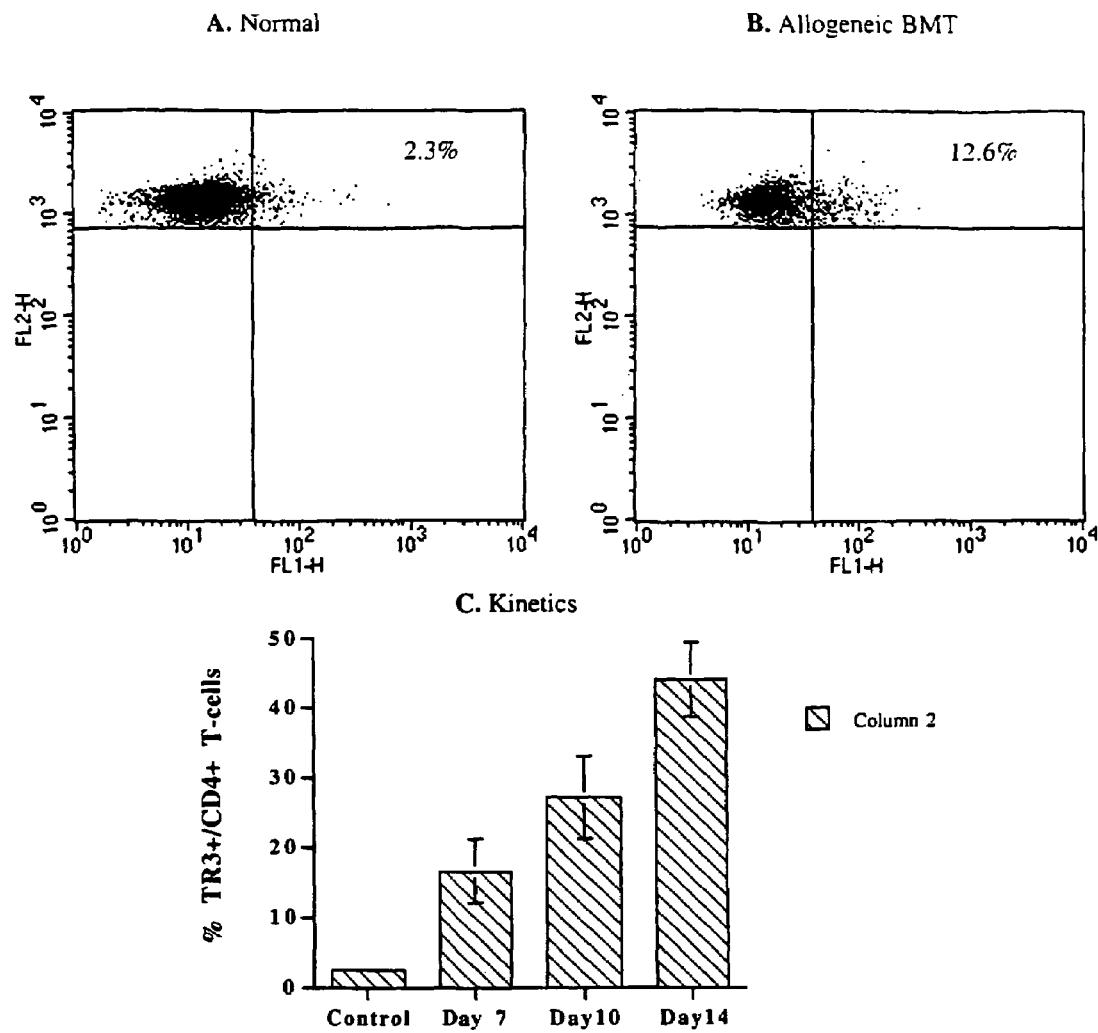

FIG. 13 shows that TR3 is expressed on CD4+ T-cells in rats that have received an allogeneic bone marrow transplant. Seven days after the allogeneic bone-marrow transplant, peripheral blood lymphocytes from a normal control (Lewis×Buffalo) F1 rat (plot A) or from a recipient of allogeneic Buffalo rat bone marrow (plot B) were collected and stained with anti-TR3:FITC (FL1) and anti-CD4:PE (FL2). Representative stains are shown in plots (A) and (B). The percentage of CD4+ T-cells expressing TR3 over time are shown in plot (C). The kinetics of TR3 expression are represented as the mean ± sd of three control rats and four rats with allogeneic BMT (bone marrow transplantation). All of the rats with allogeneic BMT developed acute GVHD.

Figure 14:
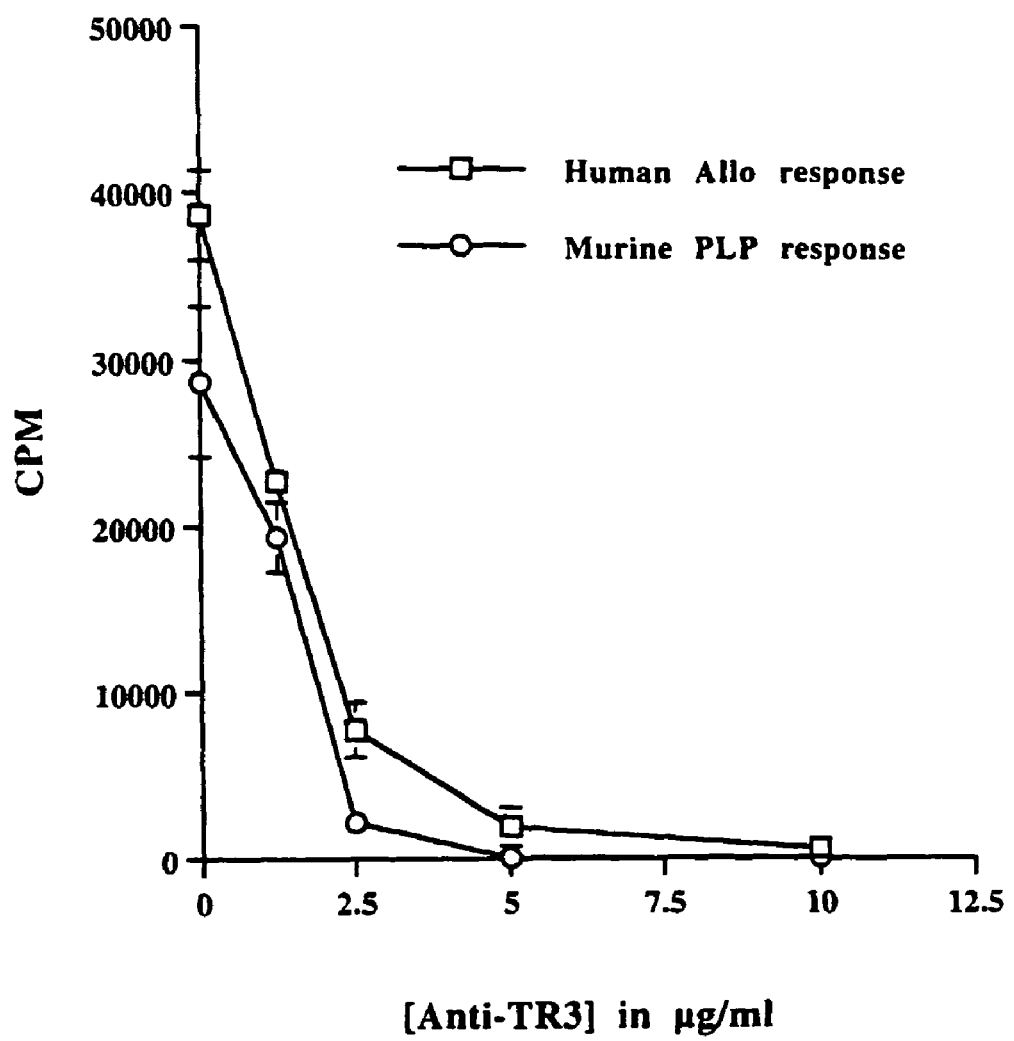

FIG. 14 shows that human and murine T-cell proliferative responses are inhibited by anti-TR3 McAbs. 20,000 T-cells from the human Allo-1 or murine PLP (139–151) cell lines were cultured with their respective antigens in the absence or presence of varying amounts of anti-TR3 McAbs. After three days the amount of incorporated $^3$H-thymidine was determined. Both T-cell lines were sensitive to the effects of the McAbs. The data represent the mean ± sd of six cultures.

Figure 15:
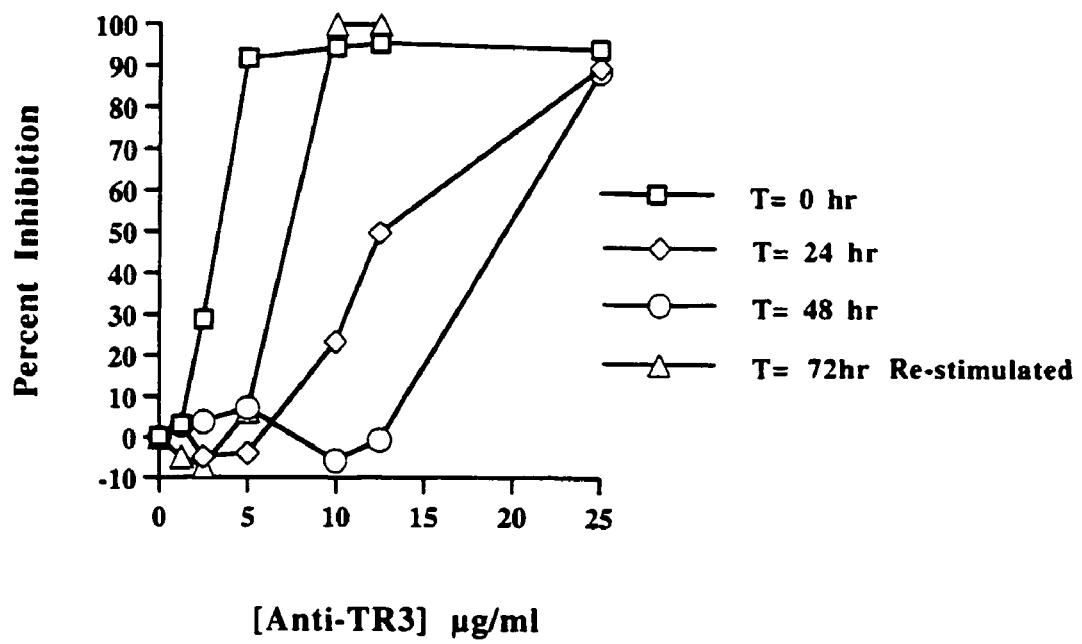

FIG. 15 shows that activated rat T-cells lose sensitivity to the inhibitory effects of anti-TR3 McAbs over time, but regain sensitivity upon reactivation with antigen at 72 hours. 20,000 MBP-specific rat T-cells (T-cells that recognize myelin basic protein) were stimulated with antigen and cultured. Anti-TR3 McAbs were added at the time indicated and assessed for $^3$H-thymidine incorporation at 72 hours. One group of cultures was re-stimulated with antigen, and anti-TR3 was also added. This latter group was assessed for $^3$H-thymidine incorporation at 120 hours. The data represent the mean of triplicate cultures. Activated T-cells lost sensitivity to anti-TR3 antibody if addition of the antibody was delayed for 24 and 48 hours post stimulation. However, the cells re-gained sensitivity upon re-stimulation at 72 hours.

Figure 16:
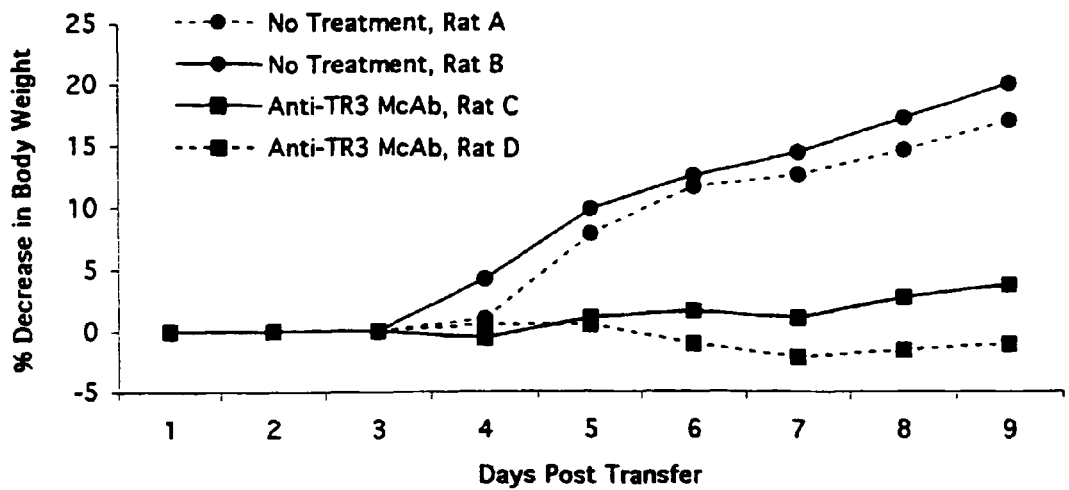
Figure 16:
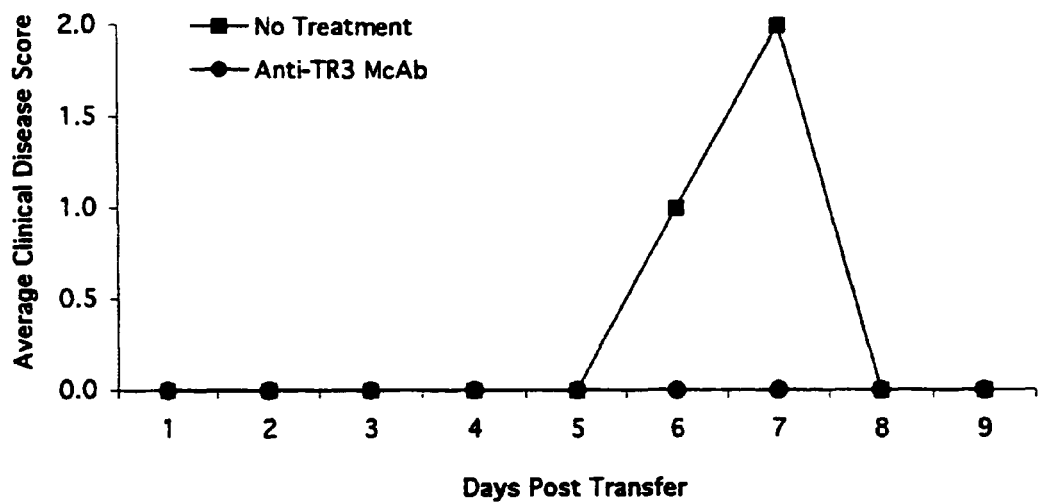

FIG. 16 shows that anti-TR3 antibody prevents subclinical and clinical adoptive transfer of EAE in rats. Four Lewis rats were injected with $2 \times 10^6$ MBP-specific T-cells to adoptively transfer EAE. Two of the rats were treated with 300 μg anti-TR3 antibody on the same day of transfer. The animals were assessed daily for subclinical weight loss (plot A). Untreated rats lost 17–20% of total body weight by day 9. Only one of the rats treated with anti-TR3 lost weight (4% weight loss). The animals were also observed for clinical EAE (plot B). Both untreated animals developed limp tails on day 6 and hind-limb paralysis on day 7, indicative of EAE. Neither of the rats given anti-TR3 immunotherapy developed any clinical signs of EAE. These data suggest that anti-TR3 is acting in vivo to eliminate T-cells that would otherwise induce EAE.

Figure 17:
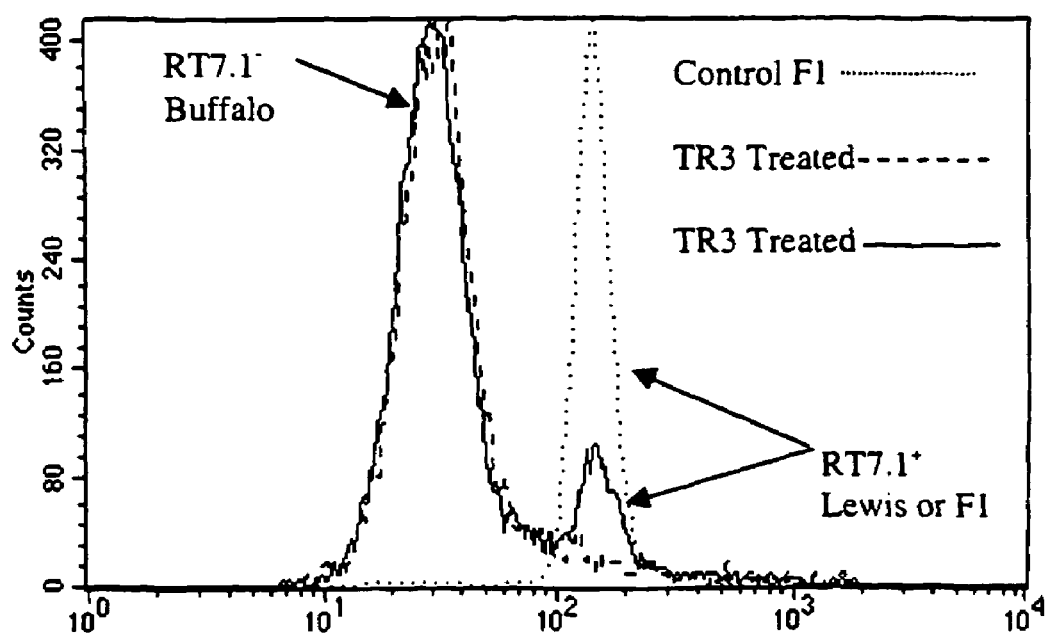

FIG. 17 shows histogram plots resulting from flow cytometry analyses set-up to select for CD4+ T-cells stained with anti-RT7.1. The data indicate that the anti-TR3-treated (Lewis×Buffalo) F1 animals were successfully reconstituted with donor-derived Buffalo CD4+ T-cells that are RT7.1−. The dashed and solid lines are respective histograms from the two Buffalo bone marrow-transplanted animals that were cured of GVHD by TR3-treatment. One animal was totally reconstituted with donor RT7.1$^{31}$ cells, while the other had 86% donor and 14% recipient T-cells.

Figure 18:
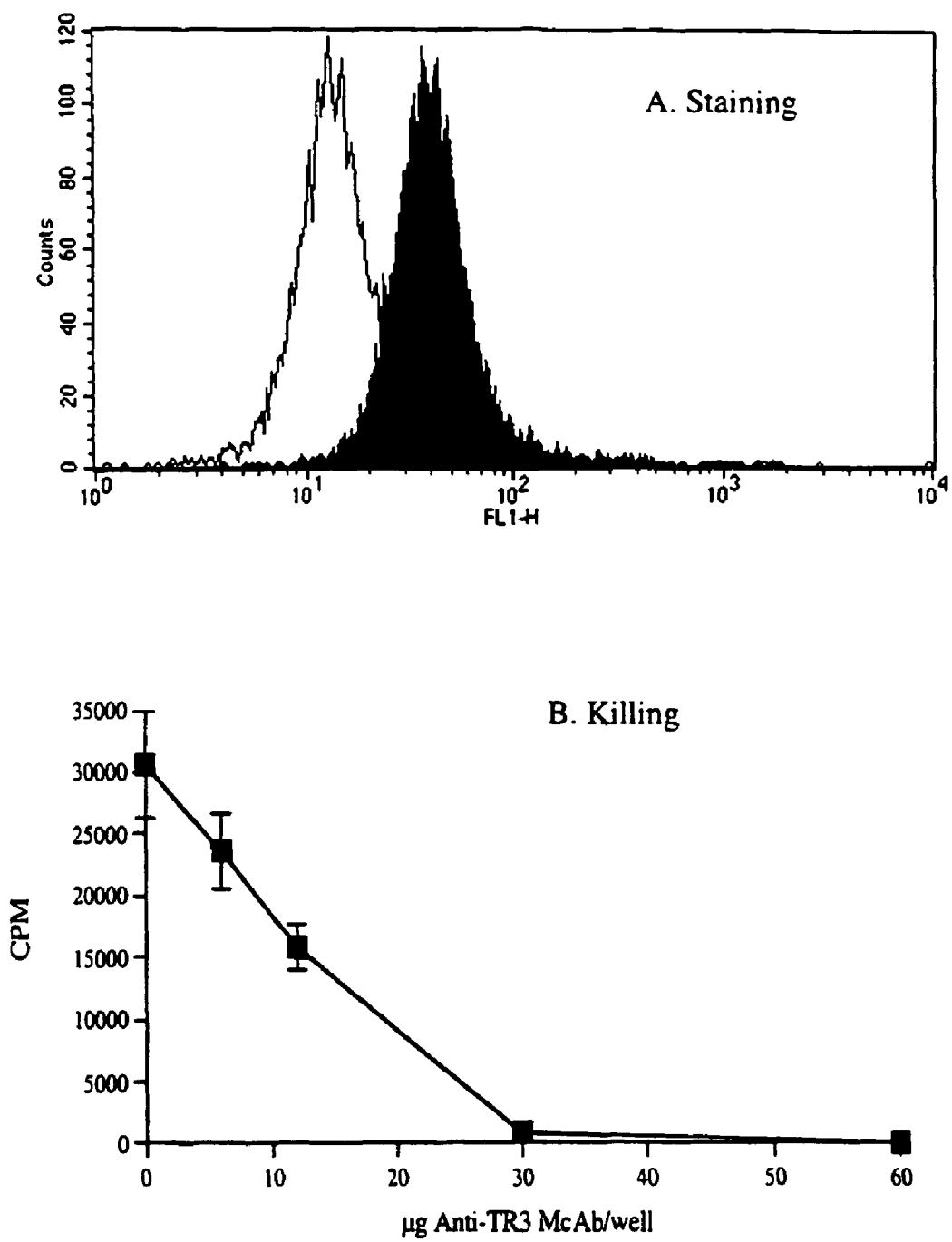

FIGS. 18(A) 18(B) show that TR3 is expressed on some tumor cells, and that McAbs to TR3 can inhibit tumor growth. Five T-cell tumor lines were stained with anti-TR3 antibody. Three murine T-lymphomas (EMG2, EFK1, and SLI) were obtained from W. R. Green (Dept. of Microbiology, Dartmouth Medical School, Lebanon N.H.). Two human T-lymphomas (HuT 78 and Jurkat) were obtained from American Type Tissue Culture (ATCC# HTB-176 and TIB-152 respectively). Four of the five tumor lines tested expressed TR3. An example of this staining is shown in FIG. 18(A). These four tumor lines were then tested for susceptibility to anti-TR3 mediated killing. All were sensitive to TR3-induced cell death as demonstrated by the representative dose-dependent inhibition curve shown in FIG. 18(B). These data suggest that T-cell tumors that express TR3 are treatable by the injection of anti-TR3 antibody.

Figure 19:
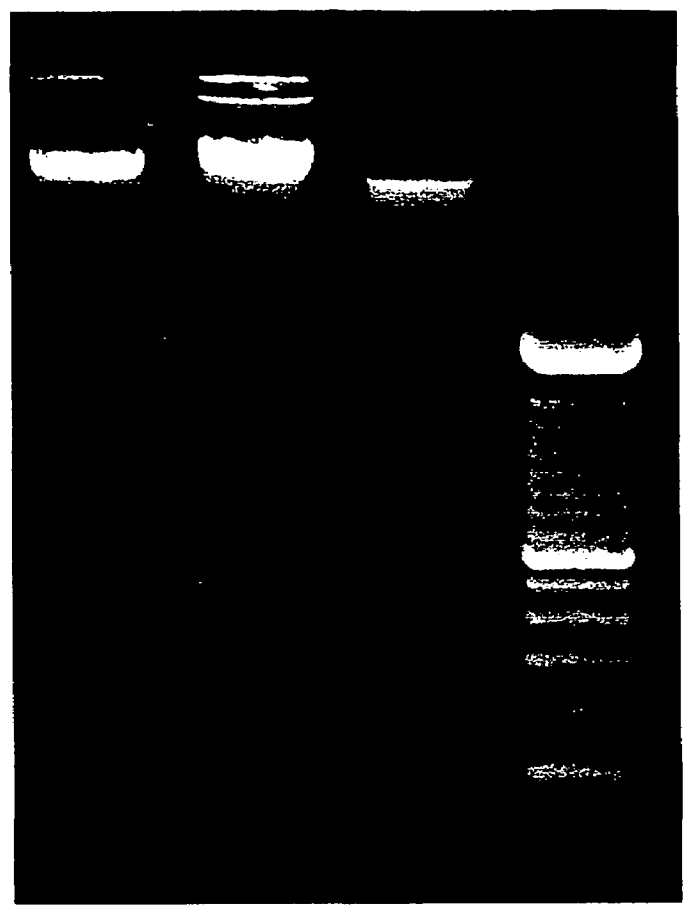

FIG. 19 shows that the mechanism of inhibition by the anti-TR3 specific monoclonal antibody is by inducing apoptosis in activated cells. Rat lymph node cells were cultured at $1 \times 10^6$ cells per ml and stimulated with Concanavalin A in the presence or absence of anti-TR3 monoclonal antibody (20 μg/ml). After 24 hours the cells were harvested and DNA extracted according to standard methods. The DNA from control and treated cells were then run on a 1% agarose gel in the presence of ethidium bromide to visualize DNA size. The characteristic DNA ladder observed in the anti-TR3 antibody treated culture is the first demonstration of apoptosis in normal T cells with anti-TR3 antibodies.

SEQUENCE LISTING

SEQ ID NO: 1 is the nucleic acid sequence of the human TR3 gene.
SEQ ID NO: 2 is the amino acid sequence of human TR3.
SEQ ID NO: 3 is the amino acid sequence of the TR3 (1–13) peptide.

SEQ ID NO: 4 is the amino acid sequence of the TR3 (1–32) peptide.

SEQ ID NO: 5 is the amino acid sequence recognized by the Lewis rat MHC class II binding cleft.

SEQ ID NO: 6 is the amino acid sequence f the murine PLP peptide.

SEQ ID NO: 7 is the amino acid sequence of the TR3 (14–32) peptide.

MODES FOR CARRYING OUT THE INVENTION

This invention provides a composition, comprising a biologically active TR3 specific binding agent that binds to TR3 and inhibits the proliferation of cells expressing TR3. In one aspect, the specific binding agent is a monoclonal antibody or a mimetic of a TR3-specific monoclonal antibody. This invention also provides a hybridoma cell line that produces the monoclonal antibody TR3 μk-1, e.g., the hybridoma cell line deposited under ATCC No. PTA-2659. The monoclonal antibody is selected from the group consisting of: at least one IgG, at leas one IgM, at least one $IgA_1$, at least one $IgA_2$, at least one IgE, at least one IgD, at least one $IgG_1$, at least one $IgG_2$, at least one $IgG_3$, and at least one $IgG_4$.

Further provided by this invention is a composition, comprising a biologically active TR3-specific binding agent that binds to TR3 and inhibits proliferation of cells expressing TR3, wherein the biologically active TR3-specific binding agent inhibits the proliferation of cells expressing TR3 by at least 30%.

This invention also provides a method for making a biologically active TR3-specific binding agent, by providing lymphoid cells from an animal that has been injected with at least one TR3-specific epitope; contacting the lymphoid cells with a TR3-specific T-cell line; fusing at least one of the lymphoid cells with at least one myeloma cell to produce a hybridoma that produces TR3 monoclonal antibody, screening the resulting monoclonal antibodies for the ability to bind to the relevant TR3 peptide; and assaying the monoclonal antibody to assess the inhibition of cells expressing TR3.

Further provided by this invention is a method for detecting biologically active TR3-specific binding agents. The method require contacting at least one TR3-specific binding agent with at least one activated T-cell or T-cell tumor, and determining a level of activated T-cell or tumor proliferation, wherein a diminution of proliferation indicates that the TR3-specific binding agent is biologically active. In one aspect, the contacting of the TR3-specific binding agent with the activated T-cell or T-cell humor occurs in vivo. In another aspect, the contacting of the TR3-specific binding agent with the activated T-cell or T-ell tumor occurs in vitro.

The binding agents identified by the above methods also are provided herein.

A method for treating a subject suspected of having a disease associated with a proliferation of cells expressing TR3 is also provided by this invention. At least one biologically active TR3-specific binding agent is delivered or administered to a subject. In one embodiment, the subject is suspected of having a T-cell mediated disease selected from the group consisting of but not limited to: autoimmune diseases such as, myasthenia gravis, systemic lupus erythematosus, rheumatoid arthritis, diabetes, multiple sclerosis, sarcoidosis, myocarditis, thyroiditis, and tumors. In another aspect, the subject is suspected of rejection of a transplanted organ, such as, heart, liver, lung, kidney, pancreas, bowel, skin, or an appendage. In an alternative embodiment, the cells expressing TR3 are T-cell leukemias or lymphomas.

I. Definitions and Abbreviations

ADCC: antibody-dependent cell-mediated cytotoxicity

AP: alkaline phosphatase, an enzyme used in colorimetric and fluorimetric ELISA detecting systems.

APC: Antigen presenting cells. These are B-cells, macrophages, dendritic cells, and some T-cells that express class II molecules and are capable of processing antigen and presenting these processed fragments to activate T-cells.

Apoptosis: any form of normal or pathological cell death characterized by a condensation and subsequent fragmentation of the cell nucleus during which the plasma membrane remains intact.

Biologically active TR3-specific binding agents: "Biologically active TR3-specific binding agents" are a subset of the specific binding agents described supra. Biologically active TR3-specific binding agents are additionally characterized by their ability to bind TR3 specifically and inhibit the proliferation of cells expressing TR3. Furthermore, the level of inhibition can vary among various different biologically active TR3-specific binding agents. Generally, a biologically active TR3-specific binding agent will inhibit the proliferation of cells expressing TR3 when compared to a negative control (a like sample without TR3-specific binding agent). Of course, some biologically active TR3-specific binding agents may exhibit greater inhibition, such as at least 30%, 40%, 50%, 60%, or 70% inhibition in a dose-dependent fashion.

BMT: bone marrow transplantation

CADD: computer-aided drug design

CD28: CD28 is a cell surface antigen expressed on T-cell subsets. CD28 is responsible for activating naïve T-cells.

CD3: CD3 is a cell surface antigen expressed on T-cells. CD3 is associated with the T-cell antigen receptor and facilitates signal transduction.

$CD4^+$: $CD4^+$ is a cell surface antigen expressed on helper T-cells, and to a lesser degree on macrophages and monocytes. $CD4^+$ acts as a co-receptor for MHC class II molecules.

$CD8^+$: $CD8^+$ is a cell surface antigen found on cytotoxic T-cells. $CD8^+$ acts as a co-receptor for MHC class I molecules.

CFA: complete Freund's adjuvant, used to augment immune responses.

ConA: Concanavalin A, a T-cell mitogen that induces activation and proliferation of T-cells.

CPM: counts per minute

EAE: experimental allergic encephalomyelitis, a model for multiple sclerosis, and other T-cell-mediated autoimmune diseases.

EBV: Epstein-Barr virus, used for transforming B-cells for long-term cell lines.

ELISA: enzyme-linked immunosorbent assay. A colorimetric or fluorimetric assay used to detect antibody binding to specific antigens.

FACS®: fluorescence-activated cell sorter (Becton Dickenson, Franklin Lakes, N.J.).

FACScan™: A FACS cell analyzer (Becton Dickenson).

FCS: fetal calf serum, a supplement for in vitro culturing of lymphocytes.

FITC: fluoresceinisothocyanate, a fluorochrome often conjugated to antibodies to detect T-cell surface antigens by flow cytometry using a FACS apparatus.

GPBP: guinea pig basic protein of myelin.

GVHD: graft-versus-host disease, a lethal T-cell-mediated disease in which donated T-cells attack the recipient's tissues.

HAT: hypoxanthine-aminopterin-thymidine (a medium used to eliminate unfused myeloma cells in hybridoma production).

LPS: lipopolysaccharide, a B-cell mitogen.

MBP: myelin basic protein, a component of myelin.

McAbs: monoclonal antibodies, antibodies from a single clone or source.

MHC class II: major histocompatibility complex (MHC) proteins responsible for presenting antigens that have been internalized for degradation in intracellular vesicles from the extracellular matrix and subsequently re-expressed on the surface for presentation to T-cells.

Mimetic: A molecule (such as an organic chemical compound) that mimics the activity of a protein, such as a monoclonal antibody that is capable of inhibiting the proliferation of cells expressing TR3. Peptidomimetic and organomimetic embodiments are within the scope of this term, whereby the three-dimensional arrangement of the chemical constituents of such peptido- and organomimetics mimic the three-dimensional arrangement of the peptide backbone and component amino acid side chains in the peptide, resulting in such peptido- and organomimetics of the peptides having substantial specific inhibitory activity. For computer modeling applications, a "pharmacophore" is an idealized, three-dimensional definition of the structural requirements for biological activity. Peptido- and organomimetics can be designed to fit each pharmacophore with current computer modeling software (using computer-assisted drug design (CADD)). See Walters, in Klegerman & Groves, eds., *Pharmaceutical Biotechnology*, Interpharm Press: Buffalo Grove, Ill., 1993, pp. 165–174; and Munson, in Munson, ed., *Principles of Pharmacology*, 1995, chapter 102, for a description of techniques used in computer-assisted drug design.

MLR: mixed lymphocyte reaction, an in vitro correlate of GVHD.

MOG: myelin oligodendrocyte glycoprotein.

MS: multiple sclerosis, a human autoimmune disease.

MUP: methylumbelliferyl phosphate, a fluorogen remaining after removal of a phosphate by a phosphatase enzyme in ELISA.

Murine PLP(139–151): the major T-cell epitope of proteolipid protein in the SJL mouse strain (amino acid sequence HCLGKWLGHPDKF (SEQ ID NO: 6); there is no signal sequence associated with PLP).

NPP: nitrophenyl phosphate, a chromogenic substrate for a phosphatase that is used in an ELISA.

Ortholog: An "ortholog" is a gene that encodes a protein displaying a function similar to a gene derived from a different species.

PAGE: polyacrylamide gel electrophoresis, a method of separating molecules on the basis of molecular size.

PBL: peripheral blood lymphocytes, lymphocytes circulating in the blood.

PBSAE: phosphate-buffered saline with sodium azide and ethylene diamine tetraacetate (EDTA).

PE: phycoerythrin, a fluorochrome-like FITC.

PLP: Proteolipid protein, a major component of the myelin sheath of the central nervous system.

RA: rheumatoid arthritis, a T-cell-mediated autoimmune disease.

RPMI 1640: Roswell Park Memorial Institute medium #1640.

RT: room temperature.

RTIB[1]: The designation for the Lewis rat MHC class II molecule.

SFM: serum-free medium.

Specific binding agents: "Specific binding agents" are agents that are capable of specifically binding to TR3. Such agents include the natural TR3 ligand(s) as well as TR3-specific immunoglobulins. The latter group (TR3-specific immunoglobulins) include, but are not limited to, polyclonal antibodies, monoclonal antibodies (including humanized monoclonal antibodies), fragments of monoclonal antibodies such as Fab, $F(ab')^2$, and Fv fragments, mimetics of TR3-specific antibodies, as well as any other agent capable of specifically binding to TR3 or fragments thereof.

Subject: The term "subject" refers to living multi-cellular vertebrate organisms, a category that includes both human and non-human mammals.

TNFR: tumor necrosis factor receptor, a prototype receptor of the TNR superfamily of receptor/ligand pairs.

TR3(1–13): a peptide of amino acids gln1–gly3 of human TR3 (amino acid sequence QGGTRSPRCDCAG (SEQ ID NO: 3)). Amino acids are numbered in accordance with the processed form of TR3, i.e., after the 24-amino acid leader sequence has been removed.

TR3(1–32): a peptide of amino acids gln1–tyr32 of human TR3 (amino acid sequence QGGTRSPRCDCAGD-FHKKIGLFCCRGCPAGHY (SEQ ID NO: 7)). Amino acids are numbered in accordance with the processed form of TR3, i.e., after the 24-amino acid leader sequence has been removed.

TR3(14–32): a peptide of amino acids asp14–tyr32 of human TR3 (amino acid sequence DFHKKIGLFC-CRGCPAGHY). Amino acids are numbered in accordance with the processed form of TR3, i.e., after the 24-amino acid leader sequence has been removed.

II. Overview of Experimental Models

The following section is provided to explain the theory behind the experiments presented below. With an understanding of the theory, the importance of the results presented are more readily apparent.

A. Use of Antigens that Fit the Lewis Rat Major Histocompatibilty Complex (MHC) Class II Binding Cleft An integral part of eliciting a peptide-specific immune response is that, in order to be immunogenic, the peptide first must be capable of binding to the MHC class II molecule. The MHC class II molecule is expressed on the surface of antigen-presenting cells (APC) which would include macrophages, B-cells, dendritic cells, and some T-cells. MHC class II molecules are thought to be primarily responsible for presenting peptides derived from proteins that have been processed in intracellular vesicles. Exogenous peptides can also be presented by surface MHC class II molecules to activate T-cells. B-cells recognize, via their receptors, foreign protein antigens and internalize the proteins. The binding of the antigen and cross-linking of multiple antigen receptors on the B-cell delivers the first activation signal. The internalized protein is then degraded into peptides and moved to the surface of the cell in association with MHC class II molecules. It is important to note that, once processed, only peptides that can associate with MHC class II molecules can be brought to the cell surface for presentation to CD4+ helper T-cells. Upon presentation of the peptide to specific T-cells, the T-cells become activated. Activated T-cells are then capable of producing cytokines that, in turn, activate B-cells for antibody production. B-cell activation is a two-signal process. The first signal is delivered upon binding specific antigen as described above. The second signal is delivered when the T-cell recognizes a peptide in association with the MHC class II molecule. After delivery of the second activation signal, the B-cells produce specific antibody.

The traditional method used to produce antibody is to immunize animals with full-length proteins. Large proteins are likely to contain both B-cell and T-cell epitopes. However, immunization with peptides (smaller portions of proteins) is unlikely to generate antibody production. The reason for this is twofold. First, most peptides do not have an ability to bind to MHC class II molecules and thus cannot be presented to T-cells. Second, most synthetic peptides are monomeric and cannot deliver the first activation signal to B-cells. Although peptides have been used to induce antibody production, the rules surrounding this method have not been detailed and peptides are most often conjugated to larger proteins for multimeric presentation to B-cells. Choosing peptides that can be presented by MHC class II molecules insures that T-cell help is provided to B-cells. In research described herein, this choice is facilitated by use of the Lewis rat.

The requirements for efficient presentation of peptides by the Lewis rat RTIB[1] class II molecule has been studied and characterized (Wegmann et. al., *J. Immunol.* 153:892–900, 1994). These studies have led to the identification of a sequence motif that predicts peptide binding to the MHC class II molecule (RTIB[1]). The RTIB[1] class II molecule will present peptides with the sequence S/TxxxxxE/D (SEQ ID NO: 5). The identification of these sequence requirements allows the selection of specific peptides to be predicted for use as T-cell antigens. Since B-cells require multivalent presentation of antigen to become activated, it is reasoned that extending the length of a peptide with a known class II binding motif provides optimal conditions for inducing antibody responses. The use of these long peptides for injection into the Lewis rat increases the probability of developing antibodies specific for the desired antigen, which in the present case is TR3. The details of this prediction and its outcome are described in section IIIA, below.

Use of TR3 peptide fragments that specifically fit into the MHC class II binding cleft of the Lewis rat, RTIB[1], allows for the efficient production of antibodies to the TR3 antigen. Once produced, these antibodies led to the discovery that TR3 is selectively expressed on activated T-cells and on some tumor cells, thereby offering therapeutic potential. This discovery has also led to the use of alternative methods for generating TR3-specific binding agents that target other regions within the TR3 amino acid sequence.

B. Creation of TR3-specific Monoclonal Antibodies

In some cases the traditional method of producing monoclonal antibodies must be modified to allow for the creation of antibodies that target molecules that normally play an integral role in the immune response. This is the case when attempting to raise antibodies to the TR3 receptor.

Normally a hybridoma is formed through the fusion of a B-cell (that is actively producing the desired antibody) and a myeloma cell. The B-cells usually originate, from a practical standpoint, from the spleen of an immunized mouse or rat. The animal is injected with the antigen in order to give rise to a primary immune response. Three days before harvesting the spleen, the animal is re-injected with the antigen. This second boost causes antigen specific B-cells and T-cells to become activated. Activated B-cells are more easily induced to fuse with a myeloma.

In the normal anamnestic or memory response, antigen-experienced B-cells interact with antigen-experienced T-cells. Both populations have been increased in number during the primary response, increasing the likelihood of fruitful interaction after the secondary challenge. Production of antibodies to proteins associated with T-cell activation, especially proteins associated with a death-domain, is a unique case.

In the present instance, the antigen is part of the TR3 receptor found on the activated T-cell surface. Therefore, as the B-cell becomes activated and starts to produce antibodies to TR3 during primary stimulation, an activated T-cell adjacent to the B-cell becomes the target for destruction. The resulting loss of circulating peptide-specific memory T-cells during the primary response decreases the availability of memory T-cells needed for the secondary response. This, in turn, decreases the probability of activating the available memory B-cell pool upon subsequent challenge. Therefore, the traditional method of activating the pool of memory B-cells prior to fusion with myeloma cells does not work in this instance. This lack of a memory response is shown below.

After this problem was identified, several alternative approaches were considered for producing monoclonal antibodies to TR3. For example, spleens from immunized animals can be removed 10, 14, or 21 days post primary immunization and then the spleen cells can be fused with myeloma cells. Alternatively, the animals can be rested for 4–6 weeks after a primary immunization, and then the spleens can be removed and further stimulated in vitro. Such stimulation can be achieved by adding lipopolysaccharide (LPS) and/or a TR3-specific T-cell line (as described below) to the spleen cells. Used in this manner, the LPS or the TR3-specific T-cell line can provide the desired extra boost of stimulation to the B-cells and increase the probability of obtaining antibody-secreting hybridomas.

C. Immunization with Complete Freund's Adjuvant (CFA)

Typically, antisera directed toward a specific antigen are raised by injection of the antigen, in combination with an adjuvant, into a suitable animal subject. An adjuvant is any substance that enhances the immune response in the animal to the antigen. Complete Freund's adjuvant (CFA) is a composition containing an oil-in-water emulsion with heat-killed mycobacteria. Subsequent to injection of the CFA and antigen, the tissue surrounding the injection sight becomes inflamed. The inflammation is, in part, attributable to the activation of T-cells. Therefore, one method of detecting a T-cell response is to assess the level of swelling at the site of injection.

D. The Experimental Allergic Encephalomyelitis (EAE)

Experimental allergic encephalomyelitis (EAE) is an experimental autoimmune disease state that can be induced in certain susceptible strains of mice and rats by the administration of myelin basic protein (MBP), proteolipid-protein (PLP), or myelin oligodendrocyte glycoprotein (MOG). In rodents, EAE is caused by the activation of $T_H1$ cells specific for MBP, MOG, or PLP. Normally about 1–3 weeks after injection of the antigen emulsified in CFA, the animal will develop encephalomyelitis (characterized by paralysis). The symptoms can be mild and self-limited, or chronic and relapsing.

It is also possible to activate antigen-specific T-cells in vitro by introducing MBP, PLP, or MOG to the T-cells. These in vitro activated T-cells can then be injected into a rat or mouse to "adoptively transfer" EAE to the recipient animal.

The EAE model is useful for testing compositions that are thought to inhibit the activity of activated T-cells. Used in this way, the test composition can be delivered to the animal. A subsequent lack of disease symptoms evident in the animal is an indication that the composition inhibits the T-cell immune response in the animal.

E. Graft-Versus-Host Disease (GVHD)

GVHD is a known complication of allogeneic bone marrow transplantation. Mature T-cells from the donated bone marrow recognize the recipient's tissue as foreign and reject it. This disease is analogous to what is observed in organ-transplantation rejection, except that, instead of rejecting one organ, the entire body of the recipient is attacked, including skin, liver, intestines, lungs, etc. GVHD can be induced in rodents by injecting parental bone marrow into F1 recipients. In this case the donated T-cells of one parent recognize the MHC of the other parent and cause GVHD. As in humans this disease is lethal in the absence of intervention. In the model described below, all non-treated recipients die by day 28 post transplant. The disease exhibited in animals that are used in the model is caused by activated T-cells, and the model represents another useful test for compositions of TR3-specific binding agents. Use of this model has demonstrated that an animal treated with TR3-specific binding agents exhibits prolongation of life (beyond 4 weeks), and a reconstitution of the recipient's immune system with the donor-derived immune system.

III. Initial Results

The data described below concerns results from experiments using TR3-specific polyclonal antisera, as well as TR3-specific monoclonal antibodies (McAbs). The data relating to the generation and use of polyclonal antisera show that the antisera can inhibit T-cell proliferation in vitro as well as in vivo. The data relating to the use of TR3-specific McAbs shows that it is possible to develop McAbs to TR3, and that the McAbs are capable of inhibiting the proliferation of activated T-cells in vitro and in vivo. The basis for these conclusions is described in detail below.

A. Selection of Peptides Fragments from Human TR3 for Use in Both Monoclonal and Polyclonal Antibody Generation The amino acid sequence of the human TR3 gene (GenBank accession number U72763) was visually scanned for the Lewis RTIB[1] class II binding motif of serine or threonine and asparagine or glutamic acid separated by five intervening amino acids (S/TxxxxxE/D). Four such motifs were found. Of these, two were in the putative extracellular domain. The first motif was located four amino acids from the amino terminus of "processed" TR3 (i.e., TR3 from which the leader amino acids 1–24 have been cleaved). The second motif was near the transmembrane region.

The first motif chosen for use as an antigen was located near the amino terminus of TR3 because this region on the native molecule is readily accessible and likely to transduce a signal. Furthermore, a synthetic peptide was used as the antigen. Because synthetic peptide synthesis occurs from the carboxy terminus to the amino terminus of the peptide, only fill-length synthetic peptides would be recognized by the MHC class II complex, allowing only full-length synthetic peptides to participate in B-cell selection, resulting in maximized T-cell help.

A 13-mer peptide and a 32-mer peptide were synthesized (gln 1 to gly 13 and gln 1 to tyr32, amino acids are numbered in accordance with the processed form of TR3, i.e., after the 24-amino acid leader sequence has been removed). When bound to the Lewis rat RTIB[1] class II binding cleft, the 1–13 peptide is predicted to be contained within the peptide binding cleft while the 1–32 peptide is predicted to present a peptide with four to five alpha helical turns outside the peptide-binding cleft.

Bodmer et al., *Immunity* 6:79–88, 1997, describes polyclonal anti-TR3 antibodies that were created by immunizing rabbits with a poorly defined "multiple antigen peptide" of oligomers of the TR3(1–23) peptide (i.e., the first 23 amino acids of the TR3(1–32) peptide). This antibody was used in Western blots to demonstrate the presence of TR3 protein in membrane extracts of various cell populations. This study did not speak to the issue of the peptide specificity of the polyclonal antibodies, and the study did not address the question of TR3 binding as a prelude to inhibition of T-cell function.

An experiment was designed to compare the immunogenicity of the TR3(1–13) peptide (gln1 to gly13) containing the MHC class II binding motif to the immunogenicity of the TR3(1–32)peptide (gln 1 to tyr32). Lewis rats (n=3) were bled and "primed" by being immunized in the footpad with 400 $\mu$g of the short peptide (TR3(1–13)) in CFA. The animals were then rested. One animal (rat 4) was immunized with the TR3(1–32) peptide as a control. Six weeks after priming, blood was obtained from the tail vein of each animal and serum prepared for analysis by fluorescence ELISA using Immulon plates (Dynatech Labs, Chantilly, Va.) coated with either the TR3(1–13) peptide, or with the TR3(1–32) peptide.

The results are shown in FIG. 1. None of the animals (rats 1–3) immunized with the TR3(1–13) peptide produced any appreciable antibody against either the TR3(1–13) peptide or the TR3(1–32) peptide. The control animal (rat 4), immunized with the TR3(1–32) peptide, exhibited a high titer of antibody that recognized the TR3(1–32) peptide and to a lesser degree the TR3(1–13) peptide.

In contrast to the lack of a humoral response, the three rats immunized with the TR3(1–13) peptide exhibited a very good T-cell response (FIG. 2). Lymph node T-cells were collected from these rats and stimulated in vitro with the TR3(1–13) peptide in a standard T-cell proliferation assay. $^3$H-thymidine was added on day two and the cells were harvested on day three to determine proliferation. T-cells from the three rats primed with the TR3(1–13) peptide exhibited a dose-dependent proliferative response to the 13-mer. This was expected because the TR3(1–13) peptide contains a known binding motif for the RTIB MHC class II molecule of the Lewis rat. These same T-cells exhibited no response to 50 $\mu$g/mL TR3(14–32), a peptide comprising amino acids 14–32 of the processed from of human TR3. This data suggested that both the 13-mer and 32-mer peptides were immunogenic for T-cells, but only the 32-mer peptide was effective at presenting a B-cell epitope.

Although the region surrounding a second human TR3 peptide (amino acids 159–165), has not been analyzed for immunogenicity, the region is expected to be immunogenic because this peptide contains an RTIB[1] class II binding motif. This motif has been used to predict peptides that can be efficiently presented by the Lewis rat RTIB[1] class II molecule. If the peptide is immunogenic for T-cells, it is likely to induce B-cells if the proper length of peptide is made. Furthermore, it may be possible to juxtapose other sequences of the TR3 molecule, or other protein sequences, next to the RTIB[1] binding motif and to raise specific antibody to regions that are adjacent to the binding motif.

B. Successful Generation of Biologically Active TR3 Polyclonal Antisera

1. Immunization

Figure 1:
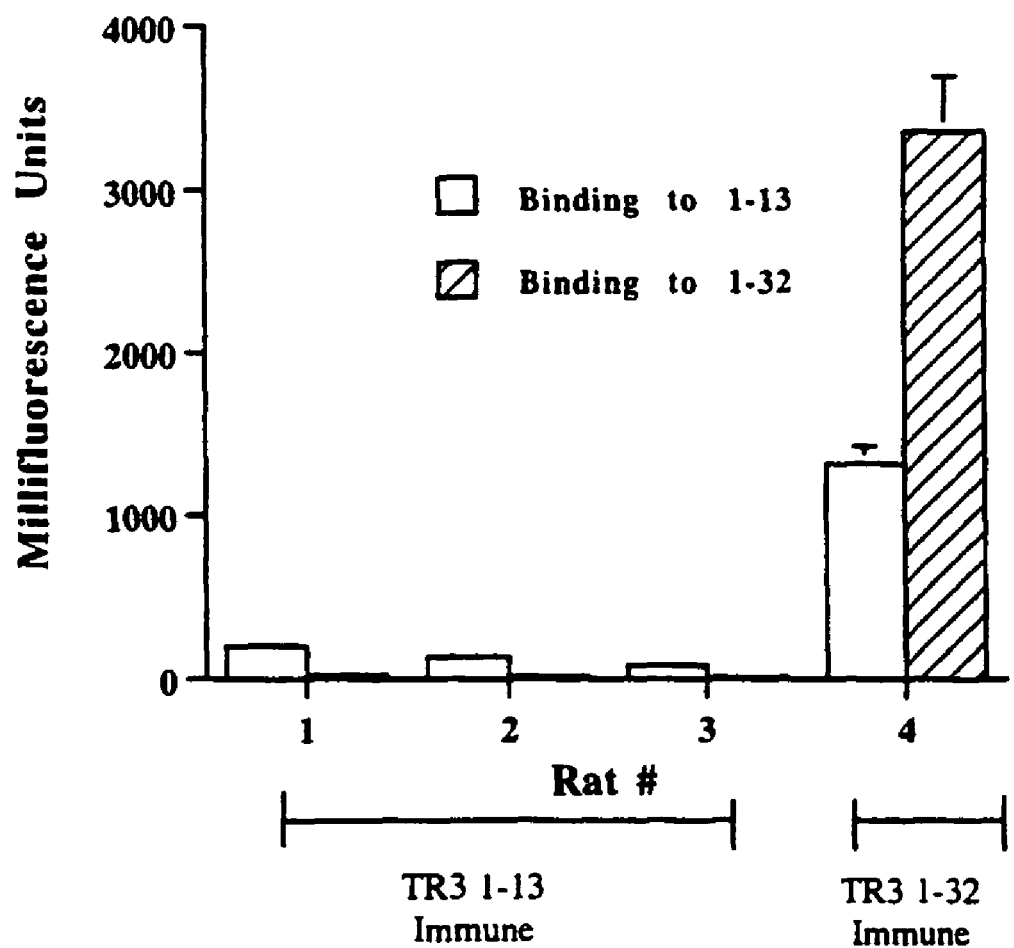
FIG. 1 shows that the first 13 N-terminal amino acids from the processed form of human TR3, the TR3(1–13) peptide, is a poor B-cell epitope. Lewis Rats 1–3 were immunized with the TR3(1–13) peptide. Lewis Rat 4 was immunized with the first 32 N-terminal amino acids from the processed form of human TR3, the TR3(1–32) peptide. Sera were collected from the rats after six weeks and assayed at a 1:5000 dilution for binding to plates coated with the TR3(1–13) peptide or the TR3(1–32) peptide using fluorescence ELISA (enzyme-linked immuno-sorbent assay). Rats 1–3 exhibited little detectable antibody against the TR3 (1–13) peptide and no detectable antibody against the TR3 (1–32) peptide. Rat 4 exhibited some reactivity against the TR3(1–13) peptide but a stronger response against the TR3(1–32) peptide. The B-cell epitope of the TR3(1–32) peptide appears to be part of a peptide associated with TR3(14–32), but outside of, the MHC (major histocompatibility complex) class II binding site.
Figure 2:
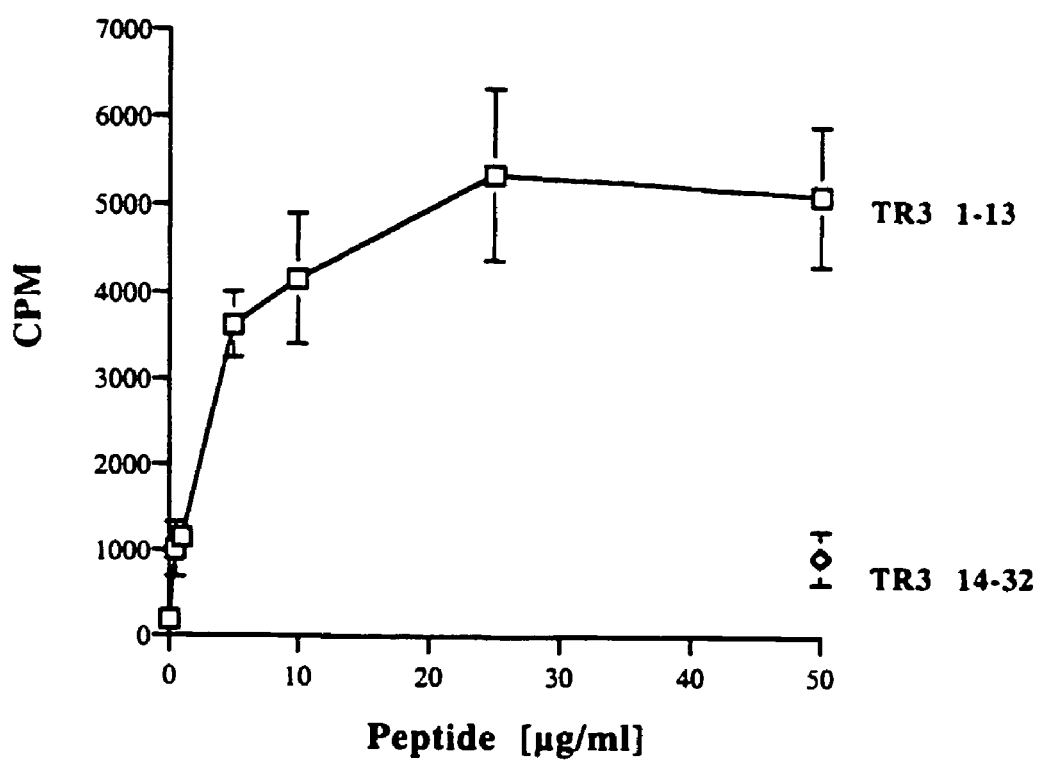
FIG. 2 shows that the TR3(1–13) peptide is immunogenic for T-cells. Lymph node T-cells from Lewis rats immunized with the TR3(1–13) peptide were challenged in vitro with the respective amounts of TR3 peptide shown. A dose-dependent response, measured by $^3$H-thymidine incorporation, to the TR3(1–13) peptide is shown, but the T-cells did not respond to a subsequent high dose of a peptide containing the N-terminal amino acids 14–32 of the processed form of human TR3, the TR3(14–32) peptide. Thus, the TR3 (1–13) peptide is immunogenic for T-cells but not B-cells.
Figure 3:
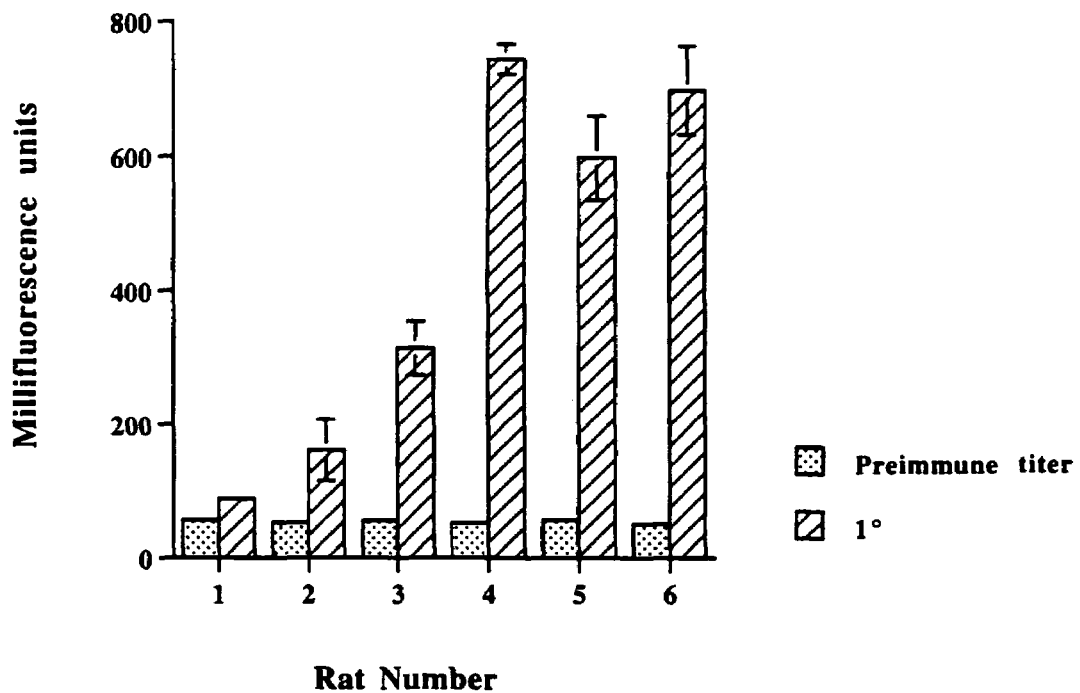
FIG. 3 shows that "priming" rats (i.e., administering a first immunogenic challenge to the rats) with the TR3 (1–32) peptide induces an immune response in the rats to TR3. Rats were immunized with the TR3 (1–32) peptide and rested for four weeks. Immune sera from the rats were assayed for TR3 (1–32) specific antibody and compared with pre-immune titers in sera from the same animal by fluorescence ELISA using TR3 (1–32) peptide-coated plates.

Lewis rats (n=6) were bled, immunized in the foot pad with 400 μg of the TR3 (1–32) peptide in CFA, and rested for one month. At one month, blood was obtained from the tail vein of each animal. Serum was prepared for analysis by fluorescence ELISA using TR3 (1–32) peptide-coated plates (for details of this procedure see below). Pre-immune serum from each animal was used as a control. The results of this first screening are shown in FIG. 3. All of the pre-immune sera exhibited background levels of antibody, i.e., 50–55 milliunits of fluorescence. After priming, two animals (rats 1 and 2) exhibited a modest (<3 fold) increase in antibodies to TR3, while four animals (rats 3–6) exhibited a 6- to 15-fold increase in antibodies that bound TR3. These data suggest that the TR3 (1–32) peptide is immunogenic and effectively presents at least one B-cell epitope.

2. Inhibition of T-cell Proliferation Using TR3-Specific Polyclonal Antisera

The sera from six rats immunized with the TR3 (1–32) peptide were tested in an ELISA assay for the ability of antibodies in the sera to bind to the TR3 (1–32) peptide. The ability of such antisera to inhibit the proliferative response of a rat myelin basic protein (MBP)-specific $CD4^+$ T-cell line was subsequently tested in vitro. 20,000 MBP-specific T-cells were cultured with a 5-fold excess of Lewis spleen cells that had been irradiated (6000 Rad) as a source of APCs and stimulated with 5 μg/mL MBP peptide. At initiation, the cultures were supplemented with either 20% or 10% serum from either TR3 immune rats or normal Lewis serum. All sera were heat-inactivated to destroy complement before use. After two days, the cultures were fed 1 μCi of $^3$H-thymidine and cultured for an additional 18–24 hours. The cultures were then harvested and $^3$H incorporation was determined by scintillation counting.

As described supra, the introduction of MBP in the presence of APCs was expected to activate the T-cells to begin expressing TR3 on their cell surface membranes. Specific binding of the TR3 antisera to the TR3 on the cell surfaces was expected to diminish substantially the growth rate of the T-cells. (A diminished growth rate is noted by a decreased incorporation of $^3$H-thymidine when compared to the control).

Figure 4:
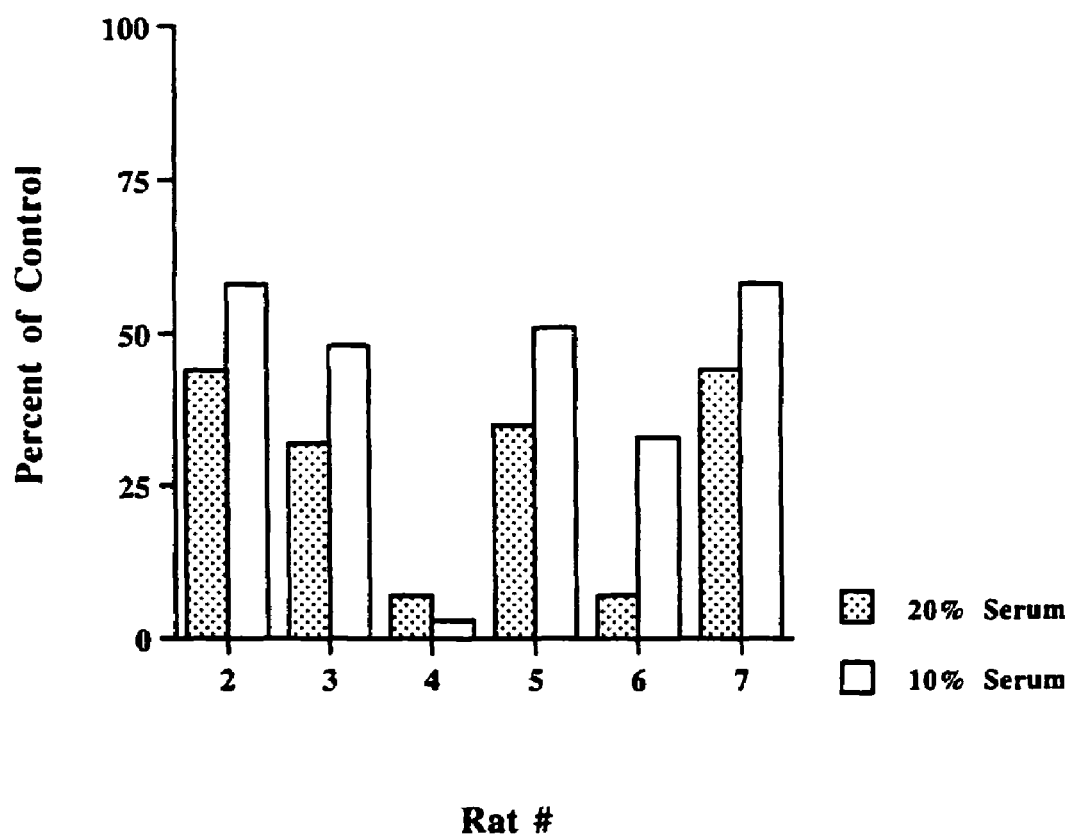
FIG. 4 shows that immune sera, obtained by immunizing rats with complete Freund's adjuvant and the TR3 (1–32) peptide, inhibited the proliferative response of a rat myelin basic protein (MBP)-specific CD4$^+$ T-cell line in vitro. Sera from six rats were tested. The sera were heat-inactivated (to eliminate the possibility of complement activity) and added to wells of a microtiter plate containing 20,000 (MBP)-specific T-cells (i.e., T-cells specific for myelin basic protein) in the presence of antigen-presenting cells and antigen. The proliferative responses were compared to that of a serum control from a non-immune Lewis rat.

The results are presented in FIG. 4 as respective percents of the control response, with the control being the appropriate normal serum culture. All six sera (rats 2–7) exhibited an inhibitory effect on the proliferation of the T-cell line. Four sera (rats 2, 3, 5, and 7) exhibited modest (50%–60%) inhibition, but in the other two (rats 4 and 6) substantial inhibition was noted. The antisera from rat 4 in FIG. 4 (same as rat 4 in FIG. 3) exhibited >95% inhibition at 10% serum. Therefore, this rat was chosen for use in subsequent experiments.

The serum from rat 4, was diluted serially (1:5, 1:10, 1:20, and 1:40) and added to T-cell cultures on day 0, day 1, day 2, and day 3 of culture, again using the MBP-specific rat T-cell proliferation assay described above. $^3$H-thymidine was added at 72 hours for days 0, 1, and 2 while, for day 3, $^3$H-thymidine addition was delayed 24 hours after the serum addition. Normal Lewis rat serum was again used as the control.

Figure 5:
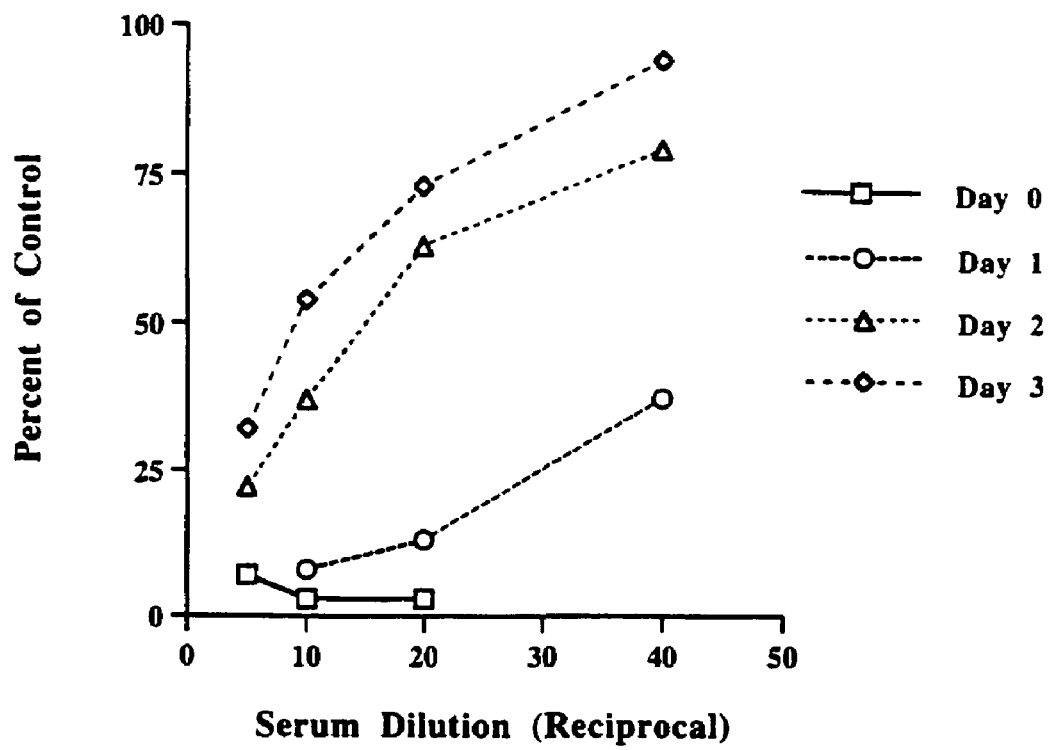
FIG. 5 shows that TR3-specific immune sera inhibit T-cell proliferation in a dose-dependent fashion. Antigen-specific T-cell proliferation is maximally inhibited by TR3 immune serum when added on day 0. Later addition of TR3 immune serum decreases the inhibitory effectiveness of the serum.

The results of this experiment are shown in FIG. 5 as percent of control vs. the reciprocal dilution, i.e., 1:10=10%, 1:40=2.5%, etc. The addition of serum on day 0 totally blocked proliferation at the 1:5, 1:10, and 1:20 serum dilutions. As expected from the results described above, the addition of serum on day 1 displayed 90% inhibition at the 1:10 and 1:20 dilutions, and the 1:40 dilution displayed >60% inhibition. Generally, the longer the delay in adding the serum to the culture, the less inhibition exhibited by the culture.

These data are consistent with the observation that mRNA (messenger ribonucleic acid) for TR3 is induced in $CD4^+$ T-cells, and that such mRNA is induced early after T-cell stimulation, after which production of the mRNA decreases. These data further imply that the observed inhibition of T-cell proliferation is biologically significant and not due to non-specific toxicity. Additionally, since complement was destroyed by prior heating, anti-TR3 antibody appears to transduce directly the inhibitory signal on antigen-responsive T-cells. Furthermore, regardless of the mechanism of the inhibitory effect, TR3 antibodies appear to be useful for treating conditions associated with the unwanted activation and proliferation of T-cells.

3. Staining of Murine $CD8^+$ T-cells with Polyclonal Antisera

Preliminary attempts to stain rat T-cells with these rat immune sera yielded cell staining but with a very high background. In order to reduce this background, murine splenocytes were used for staining. Spleens from mice were cultured for 48 hours in the presence of Concanavalin A (ConA). The cells were harvested, washed, and incubated with 10% serum from immune or control animals. The cells were then washed and stained with anti-rat Ig antibodies conjugated with fluoresceinisothiocyanate (FITC) (Sigma-Aldrich, St. Louis, Mo.). The cells were then counterstained with anti-mouse $CD8^+$ T-cell antibodies conjugated with Phycoerythrin (PE; PharMingen, San Diego, Calif.). The cells were then washed and analyzed using a fluorescence-activated cell sorter (FACScan).

Figure 6:
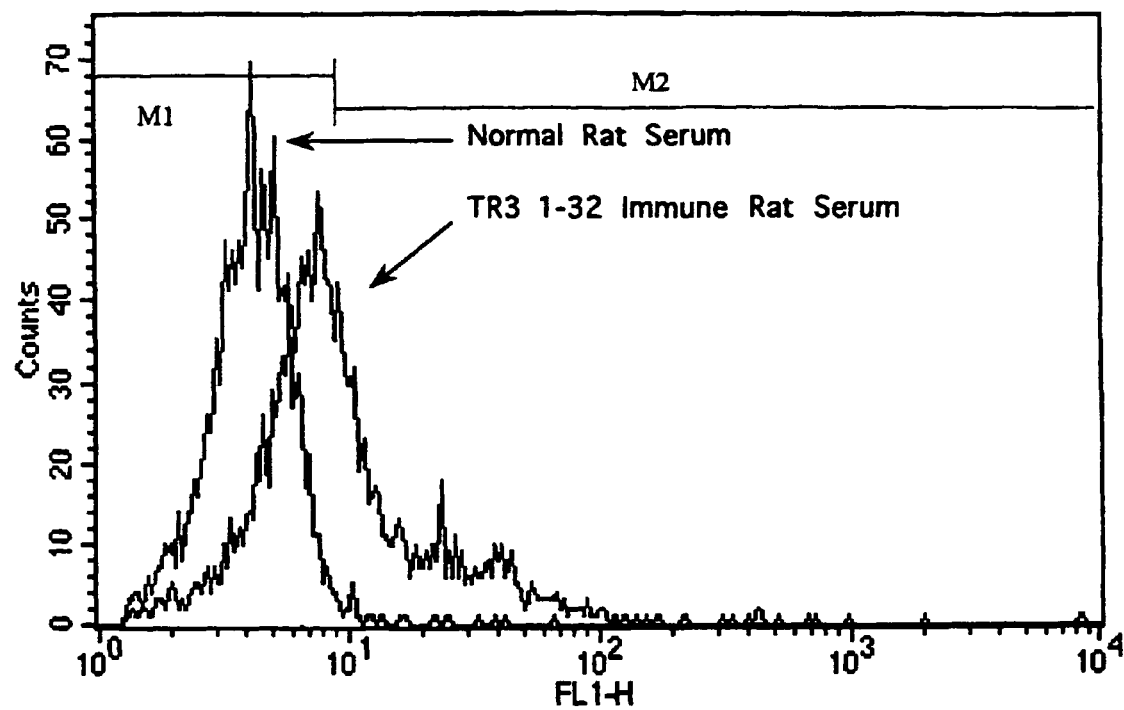
FIG. 6 depicts a flow-cytometric analysis using a FAC-Scan (Becton Dickenson, Franklin Lakes, N.J.). This analysis measures the binding of specific antibody to cell surfaces through the use of fluorescent dyes conjugated to the antibodies. Lasers are used to excite these fluorochromes in the dyes. The histogram shown in FIG. 6 shows that anti-TR3 immune serum stains activated murine CD8$^+$ T-cells. Mouse T-cells were cultured for 48 hours in the presence of Concanavalin A (ConA) to activate them, washed, and incubated with control or immune serum from rat 4 (FIG. 4). The cells were then stained with anti-rat Ig:FITC (FL1), which resulted in the staining of mouse cells bound by the rat-derived antibodies in the anti-TR3 immune serum. The mouse cells were then counterstained with CD8:PE, which resulted in the staining of all mouse cells that expressed CD8$^+$. The cell sorter was then set-up to count only cells that stained positive for CD8$^+$, some of which were double-stained for CD8$^+$ and anti-rat Ig (i.e., anti-TR3 immune sera). The left histogram, representing control mouse cells stained with normal rat serum, shows that 99% of the cells lie within the marker-1 (M1) region. The right histogram was obtained from a population of mouse cells stained with anti-TR3, and 41% of these cells shifted to the marker-2 (M2) region, indicating that the cells in the M2 region were double-stained with anti-rat Ig (i.e., anti-TR3 immune sera) and CD8:PE.

Because the inhibition data described above were obtained using $CD4^+$ T-cells, the specificity of the antiserum was tested using CD8:PE, a stain specific for $CD8^+$ cells. Thus, if the antiserum stained the $CD8^+$ cells, results from both the inhibition assay and the staining assay would collectively show that the anti-TR3 antiserum bound to both subsets of T-cells, $CD8^+$ and $CD4^+$. The results of one of three staining experiments are shown in FIG. 6. FIG. 6 shows the lack of staining using control non-immune rat serum compared with results observed with immune serum from rat 4. FIG. 6 shows a population shift indicative of staining, with 41% of the $CD8^+$ T-cells (right histogran) residing outside the region representing the control stain (left histogram). It was not surprising that the entire $CD8^+$ T-cell population shifted since the population was >99% positive for CD25 (the IL-2 receptor, an indicator of activation). Hence, a majority of the cells were activated and expressing TR3. Thus, a high proportion of the mouse $CD8^+$ T-cells became stained with anti-serum against human TR3 peptide, but not with normal rat serum.

4. In vivo inhibition of T-cells

Anti-TR3 antibodies appear to be active in vivo in suppressing T-cell function. For example, at the time of bleeding the first group of immunized animals, four of six animals immunized with the TR3 (1–32) peptide in CFA exhibited no footpad swelling or delayed-type hypersensitivity (DTH) typically associated with CFA immunization at this site. This lack of swelling is associated with the absence of activated T-cells that are usually present in inflamed tissue. Also, the ELISA experiments demonstrated that it was the four animals having the highest TR3 antibody titer that exhibited no footpad swelling. These results further suggest that the anti-TR3 antibody eliminates activated T-cells in vivo.

In view of the above, eight naïve rats were immunized in the front footpad. Four animals received CFA only and the remaining four received the TR3 (1–32) peptide in CFA. At two weeks, both groups exhibited similar footpad swelling. After one month, all animals that received only CFA still had swollen footpads. In contrast, none of the animals that received the TR3 (1–32) peptide in CFA had swollen footpads. Furthermore, three of the animals that received only CFA had adjuvant-induced arthritis in at least one hind footpad, while none of the TR3-immune animals exhibited any apparent arthritis. This accelerated decrease in footpad swelling was observed in eight out of eight animals that developed anti-TR3 antibody titers. These results illustrate the beneficial effect that TR3-specific binding agent appears to exhibit in treating T-cell mediated inflammatory disease.

Figure 7:
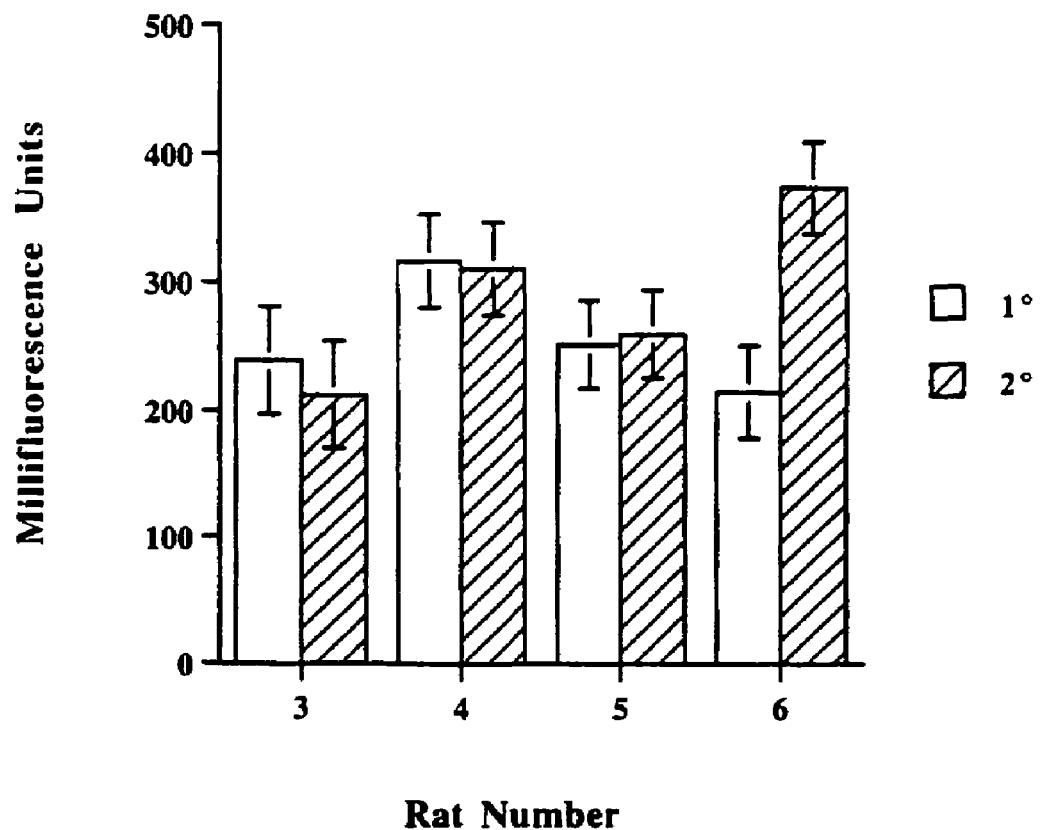
FIG. 7 shows that TR3-primed rats fail to produce an anamnestic response to the TR3 (1–32) peptide. Rats were primed with the TR3(1–32) peptide and boosted again with the TR3 (1–32) peptide six weeks later. Secondary immune sera were collected from the rats on day 10 post challenge. Primary (1°) sera, collected the day of boost, represent the titers immediately before the boost.

We also observed an apparent lack of an anamnestic or memory humoral response in animals primed with the TR3 (1–32) peptide. Typically, animals immunized with antigen and subsequently boosted with the same antigen have an anamnestic response that is characterized by a rapid increase in antibody titer and an augmented or elevated response after the booster. This is NOT the case in animals immunized with the TR3 (1–32) peptide. Four animals having a high TR3 titer were bled and then boosted with the TR3 (1–32) peptide in incomplete Freund's adjuvant and tested for an anamnestic humoral immune response ten days later. A comparison of the pre-boost titer and post-boost titer from these animals is shown in FIG. 7. Three animals (rats 3–5) exhibited no increased titer to TR3 while one (rat 6) exhibited a modest (<2-fold) increase. These data suggest that circulating anti-TR3 antibody eliminated the TR3 peptide specific T-cells capable of and necessary for providing help for the anamnestic B-cell response to TR3.

The results described above are important for four reasons. First, they suggest that multiple injections of TR3-specific binding agents can be administered as required to subjects without the complications associated with development of an immune response to the agent by the subjects. This is because any T-cell capable of responding to the TR3-specific binding agent will be functionally deleted by circulating TR3-specific binding agent.

The second important implication is more technical in nature and deals with the generation of TR3 monoclonal antibodies. As described above, the traditional method of making monoclonal antibodies to TR3 is through the use of a hybridoma. The production of the hybridoma, however, requires the presence of T-helper-cell-activated B-cells that are specific for TR3. In this case, however, TR3-specific T-cell help does not exist for a secondary immune response that would normally activate the population of antibody-expressing B-cells in vivo. Therefore, the preparation of a hybridoma must be performed using a non-traditional method.

Third, immunization with the human TR3 peptide sequence has been shown to induce antibodies that cross-react with mouse and rat T-cells. This explains why antibodies to TR3 have not been forthcoming. This has not been the case for other death-domain receptors where species-specific antibodies have been obtained. As shown below, the first monoclonal antibody against TR3 recognizes all three species.

Fourth, and equally important, the subject animals generated high titers of antibodies against self TR3 that were inhibitory both in vitro and in vivo. Nevertheless, the animals did not exhibit adverse side effects that were observed with a lethal anti-Fas antibody treatment described in the background section above.

IV. Successful Generation of Biologically Active TR3 Monoclonal Antibodies

A. Production of monoclonal antibody

As mentioned above, in order to generate a hybridoma, it is necessary to administer a second booster of antigen to the subject animal so that the population of B-cells producing antibodies in the spleen is increased prior to fusion of the B-cells with myeloma cells. However, animals injected with the TR3 (1–32) peptide for a second time fail to exhibit the appropriate boost.

Therefore, two non-traditional methods of generating monoclonal antibodies were used. The first method utilized LPS (lipopolysaccharide) to mitogenically stimulate TR3-specific B-cells in vitro before fusion. Gillis and Henney, J Immunology 126:1978–1984, 1981. The second approach was to use the TR3 (1–13) peptide-specific T-cell lines to stimulate TR3-immune B-cells in vitro. This latter method eventually achieved the successful generation of TR3-specific monoclonal antibodies.

TR3-specific T-cells were obtained from the lymph nodes of animals immune to the TR3 (1–32) peptide 10 days after priming the animals with the TR3 (1–32) peptide but before antibody to the TR3 (1–32) peptide was detectable in the animals. The T-cells were then expanded (allowed to divide) in vitro by alternating rounds of the TR3 (1–32) peptide stimulation followed by growth in tissue culture medium containing IL-2 (interleukin-2, 20 units/mL) and 10% supernatant from ConA-stimulated (for 48 hours) rat spleen cells. A spleen was removed from an animal immunized three weeks previously with the TR3 (1–32) peptide and a single-cell suspension was prepared therefrom. A mixture of the TR3 (1–32) peptide immune spleen cells ($1 \times 10^8$ cells) and TR3-specific T-cells ($3 \times 10^7$ cells) was co-cultured in the presence of TR3 (1–32) peptide (5 µg/mL). After two days the cells were washed and fused to the murine myeloma partner, FO cells (ATCC CRL-1646), at a 1:1 numerical ratio of cells. The fused cells were selected in HAT (hypoxanthine-aminopterin-thymidine) medium. Culture supernatants were assayed on the TR3 (1–32) peptide-coated plates using fluorescence ELISA. Twenty-three positive wells were found during an initial screening. Repeated cloning (6 times) in hanging-drop cultures produced one stable hybridoma determined by ELISA to produce an IgM, antibody. Hereinafter, this antibody is referred to as TR3 µk-1.

The monoclonal line was adapted to a serum-free medium (HL-1, Biowhitaker (Walkersville, Md.) and HyQ PFMab, Hyclone (Logan, Utah) worked equally well), and the TR3 µk-1 antibody was purified by concentration using an Amicon Model 402 Unit (Beverly, Mass.) equipped with a 300,000-dalton exclusion-limit filter followed by dialysis against phosphate-buffered saline. The production of antibody was assayed spectrophotometrically using 1.4 as the extinction coefficient and analyzed on a 10% polyacrylamide gel by staining with Coomassie blue. The heavy-chain band was observed at approximately 80 kD which is consistent with the size of an IgM heavy chain. Even with grossly overloaded amounts of IgM (5 and 10 µg), only minor contaminants were observable. This easy method could be used for purifying therapeutic grade anti-TR3 IgM McAbs.

One hybridoma cell line that produces monoclonal antibodies that specifically recognize and bind TR3 was deposited with American Type Culture Collection (ATCC) under Accession No. PTA 2659 and pursuant to the provisions of the Budapest Treaty on Nov. 11, 2000. The hybridoma cell line is TR3 µK-1.

B. Isotype Switching

Antibodies of various isotypes are useful for several reasons. IgM has a relatively short half-life (5–7 days) in vivo which limits the duration of the immunosuppression effected by IgM. Nevertheless, IgM antibodies have been effectively used with complement to treat bone marrow ex vivo before bone marrow transplantation with good results. For example, CAMPATH-1 is a rat IgM antibody that has been used in this fashion. (Waldmann et al., *Lancet*, 2:483–486, 1984.) CAMPATH-1 is pan-immunosuppressive because it targets a common antigen (CD52) found on B-cells, T-cells, and natural killer (NK) cells. In contrast, an IgM anti-TR3 antibody would target only activated T-cells, leaving other components of the immune system unscathed. After a short period (based on antibody half-lives) of immunosuppression, the remaining mature T-cells would be available to become effector cells. This contrasts with conventional practice in which removal of a subject from daily immunosuppressive drug therapy is followed by a lengthy period of immunosuppression during which the immune system reconstitutes itself.

The Jo2 anti-mouse Fas antibody (Ogasawara et al., *Nature*, 364:806–809, 1993) is an IgG antibody obtained from a strain of hamster termed "Armenian hamsters", and anti-human Fas antibody (PharMingen (Cifone et al., *J Exp. Med.*, 177:1547–52, 1993)) is murine IgG1. Both of these antibodies are quite effective at transducing the death signal. Hence, IgG McAbs to TR3 are probably capable of inhibiting activated T-cells.

The IgG subclasses of antibodies have a longer half-life (23 days) than IgM. Thus, use of IgG would permit a more prolonged immunosuppression. There are situations where treatment with IgG isotypes is preferred over the use of IgM. IgG penetrates tissues better than IgM, and better tissue penetration may be useful in GVHD where the skin, lung, liver, and intestines are target organs. Switching from IgM to IgG is also associated with somatic mutation (the process of DNA rearrangement that gives rise to antibody specificity), and affinity maturation (the process of preferential selection of B-cells that express antibodies that bind with high affinity to antigen). A higher-affinity antibody, such as an IgG, would normally require smaller doses for treatment and may be a better staining reagent than a lower affinity antibody, such as an IgM, for use in FACScan analysis. IgG$_2$b antibodies, (e.g., CAMPATH-1 G), are effectively immunosuppressive in vivo largely because they bind to Fc receptors and facilitate antibody-dependent cell-mediated cytotoxicity (ADCC). (However, recent studies suggest that CAMPATH may also induce apoptosis by an as yet unknown mechanism.) In vivo CAMPATH-1G is well tolerated and is potently immunosuppressive.

To determine whether Lewis rats immunized with the TR3 (1–32)peptide undergo isotype switching, sera from the TR3 (1–32) peptide-immune animals were tested for isotype-specific antibodies using fluorescence ELISA twelve weeks after priming the animals. The results of a typical assay are shown in FIG. 8. Serially diluted serum was allowed to bind to plates coated with the TR3 (1–32) peptide. After washing the plates, alkaline phosphatase (AP)-labeled antibodies against rat IgG1, IgG2a, IgG2b, or Ig were added. Pre-immune serum values of <50 millifluorescence units were obtained for each isotype (not shown). IgG1 (diamonds) and IgG2a (circles) antibodies were clearly detected above background, suggesting that both $T_H1$ and $T_H2$ type T-cells participated in the isotype switching response. IgG2b (triangles) is also present in small amounts at a 1:1000 dilution, suggesting that isotype switching does take place in vivo by priming with the TR3 (1–32) peptide. These results are consistent with the high level of T-cell help expected from MHC class II-associated peptide recognition. Presumably, isotype switching occurs before the TR3 (1–32) peptide specific helper T-cells are deleted. Alternatively, isotype switching may ensue after endogenous T-cells responding to environmental antigens express TR3, and serve as anti-TR3 memory B-cell stimulators. Regardless of the mechanism, these qualitative data demonstrate that isotype switching does occur and that it will be possible to generate monoclonal IgG antibodies, as well as the monoclonal antibodies such as IgA$_1$, IgA$_2$, IgE, IgD IgG$_1$, IgG2, IgG$_3$, and IgG$_4$. McAbs of these isotypes can serve as standards with which to quantify the humoral response to TR3 more precisely.

C. Specific Staining of T-cells with Monoclonal Antibodies

The monoclonal antibody, TR3 μl, specifically stained three different T-cell lines from three species (mouse, rat and human). Purified TR3 μk-1 McAbs were conjugated with fluoresceinisothiocyanate (FITC) for use as a direct staining reagent. For the staining assays described below, Lewis rat anti-mouse IL-2R:FITC (PharMingen clone 7D4), or Fischer rat anti-mouse Vβ14:FITC (PharMingen clone 14-2) were used as rat IgM isotype control antibodies. In some experiments, unstimulated T-cells stained with anti-TR3: FITC served as controls with essentially the same results.

The first T-cell line was a human alloreactive T-cell line (Allo-1) generated from peripheral blood lymphocytes (PBL) by repeated cycles of stimulation with an Epstein-Barr virus (EBV)-1-transformed B-cell line (EBV-1) followed by expansion in growth medium containing 10% FCS (fetal calf serum), 10% supernatant from a day-3 human MLR (Gibco BRL, Gaithersburg, Md.) supernatant, and 20 units/mL human IL-2. The Allo-1-cell line contained roughly equal percentages of both CD4 and CD8 alloreactive T-cells, and 100% of the cells became activated after stimulation with EBV-1 as determined by CD134 expression (CD134 is a cell surface antigen that is expressed on activated T-cells). The Allo-1 cell line was routinely stimulated at a 1:1 ratio with EBV-1 in RPMI 1640 (Life Technologies (GIBCO BRL), Gaithersburg, Md.) containing 2% human serum that was heat-inactivated to destroy complement before use.

The second T-cell line was a murine PLP(139–151)-specific T-cell line (Whitham et al., *J. Neurosci. Res.* 45:104–16, 1996). This line was predominantly composed of CD4$^+$ T-cells. Stimulation of this line was accomplished by incubating the cells, at a 10:1 population ratio with syngeneic thymocytes (genetically identical thymocytes that had not been exposed to PLP), in the presence of 2 μg/mL PLP(139–151) in RPMI supplemented with 1% heat-inactivated normal mouse serum.

The third T-cell line was a MBP-specific rat T-cell line that was predominantly CD4$^+$. Stimulation of this line was accomplished by incubating the cells, at a 10:1 population ratio with syngeneic thymocytes, in the presence of 2 μg/mL bovine MBP in RPMI supplemented with 1% heat-inactivated normal rat serum.

The kinetics of TR3 expression were analyzed using murine and rat CD4$^+$ T-cell lines. The rat bovine MBP-specific T-cell line was cultured at $5\times10^5$ cells/mL in the presence of $5\times10^6$ thymocytes plus 1 μg/1 mL MBP. The murine PLP-specific T-cell line was similarly stimulated, but with 2 μg/mL PLP(139–151) peptide. The cells were harvested at the given time point, washed, and stained for CD4$^+$ T-cells that expressed TR3. The results are shown in FIGS. 9(A) and 9(B) for the rat and murine cell lines, respectively.

Nearly equivalent staining of the T-cells was observed with each cell line at 24, 48, and 72 hours post stimulation, observed as a progressive population shift to the right on the FL1 axis with increasing time.

The expression level of TR3 remained consistent over the 72-hour period. This is surprising in view of the T-cell inhibition data using TR3-immune polyclonal antisera. It is therefore likely that the decreased sensitivity to TR3-mediated inhibition is not due to decreased levels of TR3 expression, but rather that the inhibitory signals through the TR3 receptor can be regulated by downstream events.

In the next staining experiment, $10^6$ human Allo-1 cells were cultured either alone or with an equal number of EBV-1 stimulator cells. The cells were harvested and stained to reveal $CD4^+$ or $CD8^+$ cells expressing TR3. Non-stimulated Allo-1 cells served as negative controls (FIGS. 10(A) and 10(B)). The data obtained 72 hours post-stimulation ("Activated") are shown in FIGS. 10(A) and 10(B) for $CD4^+$ and $CD8^+$ T-cells, respectively. As was observed for both the murine and rat T-cells, 100% of the alloreactive human $CD4^+$ and $CD8^+$ T-cells were stained with the antibody which indicated surface TR3 expression by the cells after 72 hours. Similar results were obtained after culturing the cells for 24 and 48 hours. Control cells did not stain positively for TR3. This again demonstrates that activation is required for TR3 upregulation.

Staining of rat $CD8^+$ T-cells was revealed in cultures of rat lymph node T-cells stimulated ("Activated") with anti-CD3 (10 $\mu$g/mL) and anti-CD28 (10 $\mu$g/mL) for 48 hours. These results are shown in FIGS. 11(A) and 11(B) for $CD4^+$ and $CD8^+$ T-cells, respectively. As observed with the human Allo-1 line, the vast majority of the T-cells were stained with the anti-TR3 reagent, but only after stimulation. Neither the anti-CD3 nor the anti-CD28 antibody stimulation alone was able to induce TR3 expression on these cells.

Collectively, these data show that TR3 is detectable by staining on $CD4^+$ T-cells from the human, rat, and mouse for at least 72 hrs. In addition, human and rat $CD8^+$ T-cells are also positive for TR3 expression at 72 and 48 hours, respectively (murine not tested, but see FIG. 6 above). Therefore, in an in vivo situation, the TR3 specific binding agent could bind to the target T-cell for at least 72 hours after the cell was stimulated. Furthermore, if the TR3 specific binding agent was capable of fixing complement (i.e., an IgM or IgG), it could bind to the target T-cell and initiate the complement cascade. After the complement cascade was initiated, the target T-cell would most likely be lysed and killed.

The staining of $CD4^+$ T-cells from the brains of mice and rats given adoptively transferred EAE, or from the brains of mice and rats with actively induced EAE, is shown in FIGS. 12(A)–12(D). Mice and rats were either immunized to induce active EAE (plots A and C) or given $5\times10^6$ (plot B) or $2\times10^6$ (plot D) encephalitogenic T-cells for induction of adoptive disease. The data are from day 1 of the onset of the disease in each instance. The open histograms represent the isotype control (rat anti-mouse V$\beta$14) staining of the cells. With respect to the staining of mouse cells, the control antibody strongly stained 2–3% of the T-cells, consistent with the usage of this mouse V$\beta$ gene; these data were selectively removed and, hence, not shown in the histograms. Both the rat and mouse cells display a staining characteristic of TR3 expression. The T-cells also co-stained with CD134, indicative of activated cells. These data are consistent with the data provided above showing the expression of CD134 on the vast majority of T-cells from the brains of rodents with EAE (Weinberg et al., *J. Immunol.* 162: 1818–1826, 1999).

D. Detection of Activated T-cells in the GVHD Model

We determined whether T-cells expressing TR3 could be detected in the peripheral circulation of animals after receiving allogeneic (from a non-self donor) bone marrow transplants. The results suggest that TR3 is detectable prior to disease onset, as has been demonstrated for the CD 134 T-cell activation marker. These data serve to pinpoint relevant time points for the initiation of anti-TR3 treatment in the GVHD model.

In these experiments, $20\times10^6$ bone marrow and $50\times10^6$ lymph node cells were transplanted from a Buffalo rat into each of four (Lewis×Buffalo) F1 recipients that were sublethally irradiated (600 R). Peripheral blood lymphocytes were collected on days 7, 10, and 14 post-transplantation and stained for TR3+$CD4^+$ T-cells. Peripheral blood lymphocytes from a normal F1 animal served as a control.

The percentages of double-positive T-cells (positively stained for both TR3 and CD4) obtained from a control rat and from one transplanted rat on day 7 before indications of GVHD are shown in FIGS. 13(A), and 13(B), respectively. In this depiction, called a cytogram, each dot represents a single cell. The ordinate denotes the fluorescence intensity of cells stained with CD4:PE, the stain that should identify all cells expressing CD4+. The abscissa denotes the fluorescence intensity of cells stained with TR3 $\mu$k-1, the stain that identifies cells expressing TR3. In the normal control rat, <3% of the $CD4^+$ T-cells expressed TR3. This is essentially background and is consistent with the observation that CD134 (a marker for activated T-cells) is rarely found on peripheral T-cells in normal animals. In contrast, the rat given an allogeneic bone marrow transplant seven days previously had 12% TR3$^+$ cells, a 4–5 fold increase over background. FIG. 13(C) shows the mean and standard deviation (bars) from data obtained from similar cytograms of three normal control rats and all four transplanted rats on day 7, 10, and 14 post transplantation. Normal control rats (n=3) exhibited a mean background level of 2.4±0.5 double-positive T-cells. This is consistent with the low percentages of T-cells in circulation expressing the CD134 activation marker. Rats with allogeneic bone marrow transplants exhibited elevated percentages (16.6±4.5) of double-positive cells as early as day 7. The percentages increased to 27.1±6.0 on day 10; on day 14, the percentages rose to 44.0±5.3. This rapid expansion of TR3$^+$ T-cells is similar to that reported for CD134.

The foregoing experiment can also be used to demonstrate that the TR3$^+$ T-cells are not derived from the donor. Previous use of the GVHD model has shown that CD134$^+$ T-cells collected after transplantation are alloreactive (Tittle et al., *Blood* 89:4652–8, 1997). Therefore, if the population of TR3$^+$ cells from the above experiment also express CD134, then it can be concluded that the TR3+cells are of donor origin. These data demonstrate that GVHD is a suitable model for the analysis of TR3 effects in vivo. Furthermore, it appears possible to eliminate the TR3+T-cells sufficiently early to leave >90% of the remaining T-cells untouched.

E. Inhibition of T-cell Proliferation in vitro with TR3-Specific Monoclonal Antibodies An in vitro analysis of activated-T-cell-specific killing by TR3 $\mu$k-1 was performed using 20,000 T-cells/well of human Allo-1 cells or 20,000 T-cells/well of murine PLP (139–151) peptide-specific T-cells. Six replicate wells were prepared per condition. Varying doses of TR3 $\mu$k-1 were added initially to each well. After two days, each well was fed 1 µCi of $^3$H-thymidine and cultured for an additional 18–24 hours. The cultures were then harvested and $^3$H-thymidine incorporation was determined by scintillation counting. The results of a typical experiment are shown in FIG. 14 as the mean counts per minute (CPM) as a function of the concentration of TR3 µk-1 antibody. Untreated cultures exhibited 29,000 CPM (murine) and 38,000 CPM (human). The addition of TR3 µk-1 inhibited proliferation in a dose-dependent manner with 50% inhibition ($I_{50}$) values of <2.0 µg/mL for each species. Complete inhibition of the proliferative response was attained at 5.0 µg/mL. (The observed inhibition was due to killing of the T-cells as detected by trypan blue staining. The killing may have resulted from apoptosis.) In any event, these data demonstrated that TR3 µk-1 recognized activated murine and human T-cells and transduced an inhibitory signal. Similar inhibition was also observed in antigen-specific T-cell responses using rat T-cells.

The temporal sensitivity of a rat MBP-specific T-cell line to TR3 µk-1 was assessed as described above. MBP-specific T-cells (20,000 cells/well) were re-stimulated with 1 µg MBP/mL and a 10-fold excess of irradiated syngeneic thymocytes as APCs. Varying doses of TR3 µk-1 were added at the initiation of culture, on day 1 or day 2. $^3$H-thymidine addition was added at 72 hours and the cells cultured for an additional 18–24 hours. The results are shown in FIG. 15. As demonstrated with immune sera, maximal cell killing was observed when anti-TR3 was added at the initiation of culture (squares). Less cell killing was observed with a 24-hour delay before addition of the anti-TR3 antibody (diamonds). It was even more difficult to kill cells stimulated 48 hours before addition of the antibody (circles). The $I_{50}$ (50% inhibition) values for these three treatments were roughly 3 µg/mL, 10 µg/mL and 20 µg/mL, respectively. These data are consistent with data obtained from experiments using polyclonal antisera (FIG. 5), which showed that antisera added after antigen stimulation (24, 48, and 72 hours after stimulation) were less effective at inhibiting T-cell proliferation than antisera that was added simultaneously with antigen. However, the present results differ from the polyclonal antisera data in that the present results demonstrate that, although the cells become refractory to killing, they remain sensitive so long as sufficient amounts of purified TR3 µk-1 are added.

The effect of re-stimulation with MBP (myelin basic protein) was tested also on one set of T-cell cultures. This set of cultures served to mimic an in vivo situation in which antigen stimulation is chronic, as might occur in GVHD or autoimmune disease. As shown in FIG. 15 (triangles), MBP re-stimulation apparently re-sensitized the cells to the effect of TR3 antibody shifting the kill curve to the left, indicating greater sensitivity. The $I_{50}$ value of the culture that was re-stimulated with MBP (closed triangles) was approximately 7.5 µg/mL.

These data illustrate that observed cell killing is not due to a non-specific toxic effect on the cells. Rather, the effect is biological and is mediated through the TR3 receptor on activated T-cells. The data also indicate that the cells remain susceptible if sufficient antibody were delivered, although the cells do become refractory. Unexpectedly, this refractory period is not due to loss of TR3 expression on the surface of the T-cells. This may be important because, unlike this in vitro situation, cells can also be sensitive to killing by antibody in the presence of complement in vivo. While the reason for the refractory period is unknown, it may stem from the recently discovered silencer of death domains (SODD) that has been shown to associate with the TR3 intracellular domain (Jiang et al., *Science* 253:543–546, 1999).

The data also suggest that, in cases of chronic stimulation, activated T-cells remain susceptible to TR3-mediated killing even if a non-complement-fixing antibody is used. Thus, treatment does not appear to be limited solely to prophylaxis.

Collectively, the data presented in this section demonstrate that the TR3 µk-1 antibody recognizes and kills activated human, mouse, and rat T-cells in the absence of complement, with nearly identical $I_{50}$ values for all three species.

V. TR3 McAbs Diminishes Clinical and Subclinical Symptoms in the EAE Model

The ability of the monoclonal anti-TR3 antibody to alter T-cell mediated disease was tested in an adoptive transfer EAE model system. A Lewis rat T-cell line specific for guinea pig MBP was stimulated in vitro with MBP and irradiated thymocytes as a source of antigen-presenting cells (APC:T at a 10:1 ratio). After 72 hours, the cells were washed and four Lewis rats were injected with either 1×10$^6$ MBP-specific syngenic T-cells (control), or 1×10$^6$ MBP-specific syngeneic T-cells and 300 µg TR3 µk-1 antibody. This dose would approximate the $I_{50}$ value of 3 µg/mL observed in vitro based upon an average weight of 150 g (2 mg/kg).

After being injected, the animals were assessed for subclinical weight loss and scored for clinical signs of paralysis on a daily basis. The effect of anti-TR3 antibody on subclinical disease is shown in FIG. 16(A), in which data are presented as percent decrease in body weight versus day post transfer of T-cells. The two animals that did not receive anti-TR3 µk-1 displayed significant weight loss beginning on days 4 and 5, respectively (circles). They lost 17% and 20%, respectively, of total body weight by day nine at the termination of the experiment. In contrast, one of the two animals (squares) that received TR3 µk-1 antibody slowly lost 4% of its body weight by day nine, while the other animal lost no weight during this time period.

The effect of TR3 µk-1 on clinical disease is shown in FIG. 16(B). Both animals that did not receive TR3 k-1 became obviously sick on day six (squares), grew worse on day seven, and recovered on day eight. Neither of the animals that received TR3 µk-1 (circles) showed any sign of clinical disease, consistent with the absence of subclinical weight loss. The ability to affect both clinical and subclinical EAE with a single dose of anti-TR3 treatment indicates that TR3 antibodies can be a useful treatment modality.

VI. TR3-Specific Binding Agents Cause Spontaneous Recovery In An in vivo GVHD Model Prior testing, described above (FIG. 13), showed that TR3 was expressed during acute GVHD. Such testing also indicated that GVHD could be treated with biologically active TR3-specific binding agents, such as the McAbs described supra. To test this hypothesis, four (Lewis×Buffalo) F1 rat recipients were sublethally irradiated to eliminate lymphoid cells, while sparing other tissues. With the recipients' lymphoid cells thus eliminated, 20×10$^6$ Buffalo bone marrow cells and 50×10$^6$ Buffalo lymph node cells from a donor rat were transplanted into each recipient to induce GVHD.

Each of two animals also received three injections of TR3 µk-1, on days 7, 10, and 12, post transplantation after activated T-cells were found in the peripheral circulation, as determined by the presence of CD134$^+$ T-cells and TR3-positive T-cells. A total of 4 mg TR3 µk-1 per kg body mass was injected into each of the rats. All four animals showed signs of GVDH as determined by weight loss, hair loss and other skin manifestations. Both control animals (animals not receiving TR3 μk-1 antibody) developed severe acute GVHD after transplantation and were euthanized at four weeks. The two animals treated with TR3 μk-1 underwent a spontaneous recovery beginning around day 20 as indicated by weight gain and resolution of skin abnormalities. The TR3 μk-1-treated animals continued to thrive at 16 weeks post transplantation. Hence, treatment of rats with TR3 μk-1 had a profoundly beneficial effect on acute GVHD lethality.

At 10 weeks post transplantation, the phenotype of the blood from two apparently healthy animals (that received TR3 μk-1) was tested to ascertain whether any activated T-cells were circulating, and if the circulating T-cells were derived from the donor or the recipient. This analysis was done by double staining circulating T-cells with CD134, a marker for activated T-cells, and TR3 k-1, followed by FACScan. No T-cells expressing the activation markers CD134 or TR3 were detectable. This is considered normal (see FIG. 15c, control). The animals were assessed for chimerism (the presence of donor and/or recipient T-cells) by determining the presence or absence of T-cells staining positively for RT7.1, a polymorphic allotypic marker of the leukocyte common antigen expressed on recipient T-cells, but not on Buffalo donor T-cells.

The experimental results are shown in FIG. 17. The control animal F1 that did not receive a BMT is denoted with small dotted lines; this animal produced a curve expected for cells derived from the Lewis parent of the recipient, i.e., the cells are positive. Buffalo rat-derived cells are negative and should be to the left of the F1 cells if donor cells have reconstituted the recipient. The results from the two test animals are shown by the solid line and the dashed line, respectively. The results indicate that the immune system of these two TR3 μk-1 treated animals were reconstituted with T-cells that lack the RT7.1 marker, i.e., the T-cells in these animals were donor-derived. Thus, treatment of allogeneic BMT recipients with anti-TR3 antibodies gave rise to animals with normal quiescent T-cells that were donor-derived and which were void of any GVHD symptoms.

VII. Biologically Active TR3-specific Binding Agents Kill Human Tumors Expressing TR3

Five T-cell tumors were stained (three murine T-lymphomas: EMG2, EFK1, and SLI, and two human T-lymphomas: HuT 78 and Jurkat) with TR3 TR3 μk-1:FITC. Four of the five tumor lines tested expressed TR3 (Jurkat T-cell line was negative for TR3 expression). An example of the results obtained from the staining are provided in FIG. 18(A). EFK1 stained positive for TR3 expression (filled histogram) relative to the isotype control (Rat IgM: anti-murine-Vβ14) (open histogram).

The four cells lines were then tested for susceptibility to anti-TR3 mediated killing. All TR3-positive tumors were sensitive to TR3-induced cell death as demonstrated by the representative dose-dependent inhibition for the murine EFK1 T-cell tumor shown in FIG. 18(B). These data suggest that human T-cell cancers expressing TR3 are treatable by injection of biologically active TR3-specific binding agents.

VIII. Anti-TR3 Antibodies Inhibit T cell Proliferation by Inducing Apoptosis

Rat lymph node cells (1×10⁶/ml were cultured in the presence or absence of Con A (2 μg/ml) to induce activation. One set of activated cells were also treated with anti-TR3 antibodies (10 μg/ml). After 24 hours the cells were harvested and DNA extracted for analysis on agarose gels in the presence of ethidium bromide. Identical quantities of DNA were added to each lane. The DNA from cells cultured in the absence of Con A or cultured in the presence of Con A but without anti-TR3 antibodies show a uniform DNA size of high molecular weight. In contract, DNA from the Con A activated cells grown in the presence of anti-TR3 antibodies shows a DNA laddering effect, typical of apoptosis. These results demonstrate for the first time that anti-TR3 antibodies kill activated T cells by an apoptotic mechanism.

IX. Materials and Methods

Peptide Synthesis. The TR3(1–13), TR3(14–32), and TR(1–32) peptides, the PLP(139–151) peptide, and the GPBP(70–88) peptide were synthesized using standard F-moc chemistry (Weinberg et al., *J. Immunol.* 162:1818–1826, 1999) on a model 432A peptide synthesizer (Perkin Elmer Applied Biosystems, Foster City, Calif.) according to the manufacturer's instructions. Following peptide extraction, the peptides were lyophilized and stored at −20° C. The purity of the peptides was assessed by C18 reverse-phase high-performance liquid chromatography (HPLC).

Fluorescence ELISA. The protocol for ELISA has been described previously in (Tittle, *Molecular Immunol.* 26:343–350, 1989), except that the substrate (methylumbelliferyl phosphate, MUP, Sigma-Aldrich, St. Louis, Mo.) was read fluorimetrically rather than calorimetrically as with NPP (nitrophenyl phosphate (Sigma-Aldrich, St. Louis, Mo.)). Immulon 4™ plates (Dynatech Labs, Chantilly, Va.) were coated with 1–2 μg of designated TR3 peptide per mL phosphate-buffered saline (PBS). The plates were washed with water and then blocked with 200 μL 1% gelatin in PBS containing 1 mM sodium azide to prevent non-specific binding, and 1 mM ethylene diaminetetraacetate (PBSAE). The plates were then washed three times with PBSAE and used for the assay of 50-μL volumes of serum or hybridoma culture supernatant. After incubation for two hours, the plates were washed again with PBSAE including the appropriate conjugate of anti-rat Ig and alkaline phosphatase at a 1:10,000 dilution. Wells containing anti-rat Ig were detected with a 0.2-mM concentration of MUP in a carbonate buffer, pH 8.5. After 1 hour the plates were read using a Cytofluor II instrument (PerSeptive Biosystems, Framingham, Mass.).

Inhibition of T-cell proliferation. Rat T-cells used for these assays were Lewis MBP-specific T-cell lines, Buffalo alloreactive T-cell lines, the human allo-1 T-cell line, murine PLP(139–151) peptide-specific T-cells, or normal lymph node cells. 20,000 T-cells were added to the wells of a 96-well plate and the cell lines were stimulated with antigen and irradiated (6000 Rad) stimulator cells, allostimulators, or anti-CD3 and anti-CD28. After 48 hours, $^3$H-thymidine was added and the plates were incubated for another 18–24 hours. The plates were then harvested and assessed for $^3$H-thymidine uptake using a 1205 Beta plate counter (Wallac, Gaithersburg, Md.). Human peripheral blood lymphocytes (PBL) were obtained from normal donors by venipuncture, or from the American Red Cross and processed over ficoll. The PBL cells were cultured at 50,000–100,000 cells per well in 96-well plates stimulated with 1–5 μg/mL phytohemagglutinin in vitro and assessed for inhibition by anti-TR3 McAbs of $^3$H-thymidine incorporation as described above.

Growth inhibition of T-cell lymphoma, or T-cell leukemia. Human (HuT 78 and Jurkat) and mouse (EFK1, EMG2, and SLI) T-cell tumor lines were screened for susceptibility to killing through the TR3 receptor. Tumor cells (2,000–4,000 cells/well) were added to the wells of a 96-well plate in the presence of serial dilutions of TR3 μk-1 McAb. After 24 hours, $^3$H-thymidine was added and the plates were incubated for another 18–24 hours. The plates were than harvested and assessed for $^3$H-thymidine uptake.

FACScan Analyses. McAbs against the TR3(1–32) peptide were assessed for an ability to stain activated T-cells from rat, mouse, or human sources. The T-cells were activated as described above for the proliferation experiments. For some experiments, rodent lymph node cells were stimulated with 5 μg ConA to obtain activated T-cells 24 and 48 hours later. The FACScan analysis was performed as described previously (Tittle et al., Blood 89:4652–4658, 1997). Unconjugated McAbs were detected on the cell surfaces of the rat lymphocytes using a goat anti-rat Ig FITC (KPL, Gaithersburg, Md.). All other antibodies were purchased from PharMingen (La Jolla, Calif.). Briefly, 1×10$^6$ cells were stained with an optimal amount (pre-titered) of antibody (usually 0.1–1 μg) in a total volume of 100 μL for 30 min. The cells were then washed three times in medium and diluted in 300–400 μL medium for analysis on the FACScan. For most experiments, selection was set over the lymphocyte region including the areas of high forward scatter to include activated T-cells.

Cell Fusions. The fusion protocol was based on that of Fazeka de St. Groth and Scheidegger (J. Immunological Methods 35:1–21, 1980) described previously (Tittle, Molecular Immunol. 26:343–350, 1989). In a first protocol, the spleens and lymph nodes from TR3-immunized animals having high titers of anti-TR3 antibodies were removed on days 10, 14, and 17 of the primary response. Single-cell suspensions made and the cells were fused directly with rapidly growing myeloma cells. In a second protocol, the spleens and lymph nodes of immune animals were cultured in vitro with a TR3(1–13) peptide-specific T-cell line and stimulated with 5 μg/mL TR3(1–32) peptide for two days after which the T-cells were fused to the myeloma cells. All fusions were plated out in ten 96-well plates in HAT medium. After day 4, the wells were fed every three days with fresh HAT medium. After two feedings the supernatants were kept and analyzed by ELISA for anti-TR3 reactivity. Positive wells were identified. The hybridomas were then cloned twice by hanging drop culture as described previously (Tittle, Molecular Immunol. 26:343–350, 1989).

Antibody purification. IgM antibodies were purified from serum-free medium (SFM) by concentration using an Amicon concentrator and a 300-kD exclusion limit cellulose filter. Retained antibodies were dialyzed against phosphate saline, sterilized using a 0.2-micron filter and stored at 4° C. The TR3 μk-1 antibody is produced at approximately 5 μg/mL SFM. IgG antibodies can be purified using a similar protocol, unless protein G (HyTrap, Pharmacia) proves quicker. Antibody (1 mg) was fluorescein-tagged using fluorescein isothiocyanate isomer II in 2% bicarbonate by standard methods. After incubation at room temperature (RT) overnight in the dark, non-conjugated FITC was then removed by dialysis.

T-ell lines. T-cells specific for MBP or TR3 were obtained on day 10 from a draining lymph node of rats immunized with the corresponding antigen in CFA. The lymph node cells were cultured in vitro with antigen and stimulator cells at a 1:5 ratio and cultured for 3 days. The cells were then harvested and recultured in medium containing 10% FCS (fetal calf serum) and 10% ConA supernatant. After four days, the cells were either frozen or restimulated. Murine PLP(139–151) peptide-specific T-cells were obtained in a similar manner. Human cell lines were generated against a panel of EBV-transformed B-cell stimulator lines at a 1:1 ratio. After three days the T-cells were washed and re-cultured in medium containing 20 units IL-2 and 10% of a supernatant derived from a 48-hour culture of a human MLR.

Adoptive Transfer of EAE. Lewis rat T-cell lines specific for guinea pig myelin basic protein (MBP) peptide (amino acids 72–84) and capable of transferring EAE have been established and frozen in liquid nitrogen for future use. To transfer EAE, T-cells were thawed, washed, and mixed with irradiated normal syngeneic thymocytes (as a source of antigen-presenting cells) at a ratio of 1:5. The cells are then placed in stimulation medium (RPMI 1640, 2% normal rat serum, 2 mM L-glutamine, 1 mM sodium pyruvate, 5×10$^{-5}$ M 2-mercaptoethanol) and stimulated with 1 μg/mL MBP (72–84). After 72 hours the cells were washed, counted, and injected into normal Lewis recipients. Lewis rats were injected with 1–5×10$^6$ MBP-specific T-cell blasts. The animals were then monitored every day post transfer for EAE and a clinical score for the rats was assigned as follows: 1, limp tail; 2, ataxia; 3, hindquarter paralysis; 4, quadraplegic/moribund. In each experiment the clinical EAE score was reported as an average of the score of the individuals in the group.

Induction of EAE. Active EAE is induced in the Lewis rat by injection of 100 μg guinea pig MBP peptide (amino acids 72–84) emulsified in CFA divided equally into each front foot pad. The first clinical signs of disease typically occur on days 10–12 post injection, after which the animal completely recovers. To induce active relapsing EAE, female SJL/J mice (Jackson Laboratories, Bar Harbor, Me.) were inoculated subcutaneously in the flanks at four sites with a total of 0.2 mL of emulsion of saline containing 150 μg PLP(139–151) and an equal volume of CFA containing 200 μg M. tuberculosis H37RA. Mice were examined daily by an investigator (blinded to treatment) for the development of neurological deficits. Degrees of hindlimb weakness and forelimb weakness are assessed as described (Weinberg et al., J Immunology 162:1818–1826, 1999).

X. GVHD

GVHD was induced in (Lewis×Buffalo) F1 rats after sublethal irradiation (600 Rads) by injecting 20×10$^6$ bone marrow and 50×10$^6$ lymph node cells from Buffalo donor rats. Animals were treated with anti-TR3 antibodies on days 7, 10 and 12 post transplant (100 μg/injection i.v.). All animals show signs of GVHD as determined by weight loss, hair loss and other skin manifestations. All untreated rats given such a transplant die within 4 weeks of transplant from acute GVHD.

XI. Production and Use of TR3-Specific Binding Agents

Antibodies to TR3 can play an important role in the treatment of diseases associated with the unwanted proliferation of activated T-cells. Examples of such include, but are not limited to multiple sclerosis, diabetes, rheumatoid arthritis, myesthenia gravis, myocarditis, Guillan-Barre Syndrome, systemic lupus erythematosis, autoimmune thyroiditis, dermatitis, psoriasis, Sjöbgren's Syndrome, alopecia agreata, Crohn's disease, aphthous ulcer, iritis, conjunctivitis, keratoconjunctivitis, ulcerative colitis, allergy, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves ophthalmopathy, sarcoidosis, primary biliary cirrhosis, uveitis posterior, and interstitial lung fibrosis. Antibodies developed to target TR3 can bind to the receptor in vivo, and can inhibit T-cell proliferation. Antibodies to TR3 can also be used to quantify receptor expression and help determine the relative strength of the T-cell response. This screening can be useful in determining dosage and method of therapy.

A. Production of Antibodies to TR3

Monoclonal or polyclonal antibodies may be produced to TR3, portions of TR3, or variants thereof. Optimally, antibodies raised against epitopes on these antigens will specifically detect the protein. Such specific detection requires that antibodies raised against TR3, portions of TR3, or variants thereof recognize and bind TR3, and not substantially recognize or bind to other proteins. The determination that an antibody specifically detects an antigen is made by any one of various standard immunoassay methods; for instance, the Western blotting technique (Sambrook et al., *Molecular Cloning: A Laboratory Manual*, Cold Spring Harbor, N.Y., 1989).

To determine that a given antibody preparation (such as one produced in a rat against human TR3) specifically detects TR3 by Western blotting, total cellular protein is extracted from human cells (for example, marrow stromal fibroblasts) and electrophoresed on a sodium dodecyl sulfate-polyacrylamide gel. The proteins are then transferred to a membrane (for example, nitrocellulose) by Western blotting, and the antibody preparation is incubated with the membrane. After washing the membrane to remove non-specifically bound antibodies, the presence of specifically bound antibodies is detected by using an anti-rat antibody conjugated to an enzyme such as alkaline phosphatase. Application of the substrate 5-bromo-4-chloro-3-indolyl phosphate/nitro blue tetrazolium results in the production of a dense blue compound by immuno-localized alkaline phosphatase.

Antibodies that specifically detect TR3 will, by this technique, be shown to bind substantially only the TR3 band (which will be localized at a given position on the gel as determined by the molecular weight of TR3). Non-specific binding of the antibody to other proteins may occur and may be detectable as a weaker signal on the Western blot (which can be quantified by automated radiography). The non-specific nature of this binding will be recognized by one skilled in the art by the weak signal obtained on the Western blot relative to the strong primary signal arising from the specific anti-TR3 binding.

Antibodies that specifically bind to TR3 belong to a class of molecules that are referred to herein as "specific binding agents." Specific binding agents that are capable of specifically binding to TR3 include polyclonal antibodies, monoclonal antibodies (including humanized monoclonal antibodies), and fragments of monoclonal antibodies such as Fab, F(ab')2, and Fv fragments, as well as any other agent capable of specifically binding to the epitopes on the proteins, for example soluble constructs of the putative TR3 ligand(s).

Substantially pure TR3 suitable for use as an immunogen can be isolated from suitable cell cultures, or synthesized as described above. Concentration of TR3 protein in the final preparation is adjusted, for example, by concentrating, using an Amicon filter device, to a few micrograms per milliliter. Alternatively, peptide fragments of TR3 may be utilized as immunogens. Such fragments may be chemically synthesized using standard peptide synthesis methods, or may be obtained by cleavage of entire TR3 molecules followed by purification of the desired peptide fragments. Peptides as short as three or four amino acids in length are immunogenic when presented to the immune system in the context of a Major Histocompatibility Complex (MHC) molecule, such as MHC class I or MHC class II. Accordingly, peptides comprising at least three (preferably at least four, five, six, or more) consecutive amino acids of the disclosed TR3 amino acid sequence may be employed as immunogens to raise antibodies.

Because naturally occurring epitopes on proteins are frequently comprised of amino acid residues that are not adjacently arranged in the peptide when the peptide sequence is viewed as a linear molecule, it may be advantageous to utilize longer peptide fragments from the TR3 amino acid sequences in order to raise antibodies. Thus, for example, peptides that comprise at least 10, 15, 20, 25, or 30 consecutive amino acid residues of the amino acid sequence may be employed. Monoclonal or polyclonal antibodies to intact TR3, or to peptide fragments thereof, may be prepared as described below.

B. Monoclonal Antibody Production by Hybridoma Fusion

Monoclonal antibody to epitopes of the TR3, which are identified and isolated as described above, can be prepared from murine hybridomas according to the classical method of Kohler and Milstein, *Nature* 256:495, 1975, or derivatives or variations thereof. As described above, the use of the classical method without a modification to accommodate the lack of T-cell help available, will not efficiently allow for the creation of hybridomas. However, it is possible that, after repeated attempts using the Kohler & Milstein method, a hybridoma might be created that secretes TR3 monoclonal antibodies. Briefly, a mouse is repetitively inoculated with a few micrograms of the selected protein over a period of a few weeks. The mouse is then sacrificed, and the antibody-producing cells of the spleen isolated. The spleen cells are then fused by means of polyethylene glycol with mouse myeloma cells, and the excess unfused cells destroyed by growth of the system on a selective medium (HAT medium) comprising aminopterin. The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Enzymol* 70:419, 1980), and derivative methods thereof. Selected positive clones can be expanded and their monoclonal antibody product harvested for use. Detailed procedures for monoclonal antibody production are described in Harlow and Lane, *Antibodies, A Laboratory Manual*, Cold Spring Harbor Laboratory, New York, 1988. In addition, protocols for producing humanized forms of monoclonal antibodies (for therapeutic applications) and fragments of monoclonal antibodies are known in the art.

C. Antibodies Raised by Injection of TR3 cDNA

Antibodies may be raised against TR3 or fragments thereof by subcutaneous injection of a DNA vector that expresses TR3 or fragments thereof into laboratory animals, such as mice. Delivery of the recombinant vector into the animals may be achieved using a hand-held form of the Biolistic system (Sanford et al., *Particulate Sci. Technol.* 5:27–37, 1987 as described by Tang et al., *Nature* (London) 356:153–154, 1992). Expression vectors suitable for this purpose may include those that express TR3 or fragments thereof under the transcriptional control of either the human β-actin promoter or the cytomegalovirus (CMV) promoter.

Methods of administering naked DNA to animals in a manner to cause expression of that DNA in the body of the animal are well known and are described, for example, in U.S. Pat. No. 5,620,896 ("DNA vaccines against rotavirus infections"), U.S. Pat. No. 5,643,578 ("Immunization by inoculation of DNA transcription unit") and 5,593,972 ("Genetic immunization"), and references cited therein.

D. Antibody Fragments

Antibody fragments may be used in place of whole antibodies and may be readily expressed in prokaryotic host-cells. Methods of making and using immunologically effective portions of monoclonal antibodies, also referred to as antibody fragments, are well known and include those described in Better and Horowitz, *Methods Enzymol* 178: 476496, 1989; Better et al., in Streilein et al., eds., *Advances in Gene Technology: The Molecular Biology of Immune Disease &the Immune response (ICSU Short Reports)*, 10:105, 1990. Glockshuber et al., *Biochemistry* 29:1362–1367, 1990; and U.S. Pat. No. 5,648,237 ("Expression of Functional Antibody Fragments"), U.S. Pat. No. 4,946,778 ("Single Polypeptide Chain Binding Molecules"), and 5,455,030 ("Immunotherapy Using Single Chain Polypeptide Binding Molecules"), and references cited therein.

E. Humanized Antibodies

Humanized monoclonal antibodies may be preferred in clinical applications. Methods of making humanized monoclonal antibodies are well known, and include those described in U.S. Pat. No. 5,585,089 ("Humanized Immunoglobulins"), U.S. Pat. No. 5,565,332 ("Production of Chimeric Antibodies—A Combinatorial Approach"), 5,225,539 ("Recombinant Altered Antibodies And Methods Of Making Altered Antibodies"), 5,693,761 ("Polynucleotides Encoding Improved Humanized Immunoglobulins"), 5,693,762 ("Humanized Immunoglobulins"), 5,585,089 ("Humanized Immunoglobulins"), and 5,530,101 ("Humanized Immunoglobulins") and references cited therein.

F. Human Antibodies

Recently, a large portion of the human immunoglobulin (Ig) locus was transgenically placed into mice with the murine Ig locus knocked out (Mendez et al., *Nature Genetics* 15:146–156, 1997). By using class II binding motifs known for the H-2 b background of these animals, it may be possible to raise human anti-TR3 antibodies. It may also be possible to raise human anti-TR3 antibodies by immunizing these animals with purified human TR3 peptide or fragments thereof. Such antibodies would be the preferred reagent for human clinical use.

XII. Delivery of the Biologically Active TR3-Specific Binding Agents

For administration to animals, purified biologically active TR3-specific binding agents are generally combined with a pharmaceutically acceptable carrier. Pharmaceutical preparations may contain only one biologically active TR3-specific binding agent, or a mixture of several biologically active TR3-specific binding agents. The pharmaceutical preparations may also include fragments of TR3-specific binding agents, or multiple different fragments of TR3-specific binding agents. In general, the nature of the carrier will depend on the particular mode of administration being employed. For instance, parenteral formulations usually comprise injectable fluids that include pharmaceutically and physiologically acceptable fluids such as water, physiologi cal saline, balanced salt solutions, aqueous dextrose, glycerol, human albumin or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH-buffering agents and the like, for example sodium acetate or sorbitan monolaurate.

As is known in the art, certain protein-based pharmaceuticals are delivered inefficiently by ingestion. However, pill-based forms of pharmaceutical proteins alternatively may be administered subcutaneously, particularly if formulated in a slow-release composition. Slow-release formulations may be produced by combining the target protein with a biocompatible matrix, such as cholesterol. Another possible method of administering protein pharmaceuticals is through the use of miniature osmotic pumps. A biocompatible carrier would also be used in conjunction with this method of delivery.

It is also contemplated that biologically active TR3-specific binding agents and fragments thereof be delivered in the nucleic-acid form to cells and subsequently translated by the host-cell. This could be done, for example, by using viral vectors or liposomes. Liposomes can also be used for the delivery of the protein itself.

The pharmaceutical compositions of the present invention may be administered by any means that achieve their intended purpose. Amounts and regimens for the administration of biologically active TR3-specific binding agents, can be determined readily by those with ordinary skill in the clinical art of treating diseases associated with unwanted T-cell activation. For use in treating these conditions, the described biologically active TR3-specific binding agents are administered in an amount effective to inhibit T-cell proliferation. The antibodies and/or fragments thereof may be administered to a host in vivo, e.g., through systemic administration, such as intravenous or intraperitoneal administration. Also, the antibodies and/or fragments thereof may be administered intralesionally: i.e., the antibody may be injected directly into the affected area, such as the site of a graft in the case of organ transplantation.

Effective doses of biologically active TR3-specific binding agents will vary depending on the nature and severity of the condition to be treated, the age and condition of the subject, and other clinical factors. Thus, the final determination of the appropriate treatment regimen will be made by an attending clinician. Typically, the dose range will be from about 0.1 $\mu$g/kg body weight to about 100 mg/kg body weight. Other suitable ranges include doses of from about 1 $\mu$g/kg to 10 mg/kg body weight. The dosing schedule may vary from once a week to daily, depending on a number of clinical factors, such as the subject's sensitivity to the protein. Examples of dosing schedules are 3 $\mu$g/kg administered twice a week, three times a week or daily; a dose of 7 $\mu$g/kg twice a week, three times a week or daily; a dose of 10 $\mu$g/kg twice a week, three times a week, or daily; or a dose of 30 $\mu$g/kg twice a week, three times a week, or daily. In the case of a more aggressive disease it may be preferable to administer doses such as those described above by alternate routes including intravenously or intrathecally.

Continuous infusion may also be appropriate.

As mentioned above, anti-TR3 antibodies and other binding agents according to the invention will be useful for the treatment of diseases associated with unwanted activation of T-cells. Examples of such disease are, multiple sclerosis, rheumatoid arthritis, sarcoidosis, myocarditis, acute and chronic rejection diseases (GVHD, organ transplant rejection), myasthenia gravis, diabetes, delayed-type hypersensitivity, allergy, toxic shock syndrome and cancer (lymphoma or leukemia).

Having illustrated and described the principles of the invention in multiple embodiments and examples, it should be apparent to those skilled in the art that the invention can be modified in arrangement and detail without departing from such principles. We claim all modifications coming within the spirit and scope of the following claims.

What is claimed is:

1. A composition, comprising a biologically active TR3-specific binding antibody that binds to TR3 and inhibits the proliferation of activated lymphocytes expressing TR3.

2. The composition of claim 1, wherein the antibody is a monoclonal antibody.

3. A hybridoma cell line that produces the monoclonal antibody of claim 2.

4. The hybridoma cell line of claim 3, wherein the cell line is ATCC No. PTA-2659.

5. The composition of claim 2, wherein the monoclonal antibody is selected from the group consisting of: at least one IgG, at least one IgM, at least one $IgA_1$, at least one $IgA_2$, at least one IgE, at least one IgD, at least one $IgG_1$, at least one $IgG_2$, at least one $IgG_3$, and at least one $IgG_4$.

6. A composition, comprising a biologically active TR3-specific antibody that binds to TR3 and inhibits proliferation of cells expressing TR3, wherein the biologically active TR3-specific binding agent inhibits the proliferation of cells expressing TR3 by at least 30%.

7. The composition of claim 1, wherein the activated lymphocytes are activated T-cells.

8. A method for making a biologically active TR3-specific, monoclonal antibody comprising:
    providing lymphoid cells from an animal that have been primed or immunized with at least one TR3-specific epitope in vivo;
    contacting the lymphoid cells with a TR3-specific stimulated T-cell line to provide adequate T-cell help;
    activating the mixture of cells in vitro with an effective amount of TR3-specific epitope and IL-2;
    fusing at least one of the lymphoid cells with at least one myeloma cell, to produce a hybridoma that produces TR3 monoclonal antibody;
    screening the resulting monoclonal antibodies for the ability to bind to the relevant TR3 peptide; and
    assaying the monoclonal antibody to assess the inhibition of activated T-cells expressing TR3.

9. A biologically active TR3-specific monoclonal antibody produced by the method of claim 8.

10. A method for detecting biologically active TR3-specific binding agents, comprising:
    (a) contacting at least one compound with TR3 and assessing binding;
    (b) contacting at least one TR3-specific binding agent with at least one activated T-cell or T-cell tumor; and
    (b) determining a level of activated T-cell or tumor proliferation, wherein a lack of proliferation indicates that the TR3-specific binding agent is biologically active.

11. The method of claim 10, wherein the biologically active TR3-specific binding agent is a ligand.

12. The method of claim 10, wherein contacting the TR3-specific binding agent with the activated T-cell or T-cell tumor occurs in vivo.

13. The method of claim 10, wherein contacting the TR3-specific binding agent with the activated T-cell or T-cell tumor occurs in vitro.

14. The method of claim 10 wherein the specific binding agent is a mimetic of a TR3-specific monoclonal antibody.

* * * * *